(12) United States Patent
Lu et al.

(10) Patent No.: US 9,012,622 B2
(45) Date of Patent: Apr. 21, 2015

(54) COMPOSITIONS AND METHODS USING SIRNA MOLECULES AND SIRNA COCKTAILS FOR THE TREATMENT OF BREAST CANCER

(76) Inventors: Patrick Y. Lu, Rockville, MD (US); David Evans, North Potomac, MD (US); Jun John Xu, Germantown, MD (US)

(*) Notice: Subject to any disclaimer, the term of this patent is extended or adjusted under 35 U.S.C. 154(b) by 18 days.

(21) Appl. No.: 13/141,122

(22) PCT Filed: Dec. 31, 2009

(86) PCT No.: PCT/US2009/069950
§ 371 (c)(1),
(2), (4) Date: Nov. 26, 2011

(87) PCT Pub. No.: WO2010/078517
PCT Pub. Date: Jul. 8, 2010

(65) Prior Publication Data
US 2012/0071540 A1    Mar. 22, 2012

Related U.S. Application Data

(60) Provisional application No. 61/142,148, filed on Dec. 31, 2008.

(51) Int. Cl.
*C07H 21/04* (2006.01)
*C12N 15/113* (2010.01)

(52) U.S. Cl.
CPC .......... *C12N 15/113* (2013.01); *C12N 15/1135* (2013.01); *C12N 15/1136* (2013.01); *C12N 15/1137* (2013.01); *C12N 15/1138* (2013.01); *C12N 2310/11* (2013.01); *C12N 2310/113* (2013.01); *C12N 2310/17* (2013.01); *C12N 2320/31* (2013.01); *C12N 2320/32* (2013.01)

(58) Field of Classification Search
CPC .................................................. C12N 2310/14
See application file for complete search history.

(56) References Cited

U.S. PATENT DOCUMENTS

| 2005/0176024 A1 | 8/2005 | McSwiggen et al. | |
| 2006/0025366 A1* | 2/2006 | MacLachlan et al. | 514/44 |
| 2006/0121514 A1 | 6/2006 | Young et al. | |
| 2006/0134787 A1 | 6/2006 | Zamore et al. | |
| 2006/0265765 A1 | 11/2006 | Agatsuma et al. | |
| 2007/0003519 A1 | 1/2007 | Lu et al. | |
| 2008/0241198 A1 | 10/2008 | Lui et al. | |
| 2008/0279920 A1 | 11/2008 | Tang et al. | |
| 2010/0319074 A1 | 12/2010 | Lu et al. | |
| 2011/0165227 A1* | 7/2011 | Yan et al. | 424/450 |

FOREIGN PATENT DOCUMENTS

| WO | WO 0147496 A1 | 7/2001 |
| WO | WO 03040399 A2 | 5/2003 |
| WO | WO 03070918 A2 | 8/2003 |
| WO | WO 03090719 A1 | 11/2003 |
| WO | WO 2005076999 A2 | 8/2005 |
| WO | WO 2007079224 A2 | 7/2007 |

OTHER PUBLICATIONS

Lee et al. (PLOS medicine, Jun. 2007, vol. 4: 1101-1116).*
International Preliminary Report on Patentability of the International Bureau of WIPO on International App. No. PCT/US2009/069950 (WO 2010/078517) of Sirnaomics, Inc., Jul. 5, 2011.
International Search Report of the ISA/US on International App. No. PCT/US2009/069950 (WO 2010/078517) of Sirnaomics, Inc., Aug. 3, 2010.
Cheema, Sangeeta, et al., "Regulation and Guidance of Cell Behavior for Tissue Regeneration Via the Sirna Mechanism", Wound Repair and Regeneration, vol. 15, No. 3, 2007, pp. 286-295.
De Wolf, Holger, et al., "Effect of Cationic Carriers on the Pharmacokinetics and Tumor Localization of Nucleic Acids after Intravenous Administration," International Journal of Pharmaceutics, 331, 2007, pp. 167-175.
Leng, Qixin, et al., "Highly Branched HK Peptides Are Effective Carriers of siRNA," The Journal of Gene Medicine, 2005, 7, pp. 977-986.
Pickering, Lulu, "Progress in RNA-based therapeutics," Spectrum Drug Discovery and Design, Decision Resources, Inc., Waltham, Massachusetts, Aug. 4, 2005, pp. 6-1 to 6-20.
Whitmore, Mark, et al., "Synergistic Activation of Innate Immunity by Double-Stranded RNA and CpG DNA Promotes Enhanced Antitumor Activity," Cancer Research 64, 5850-5860, Aug. 15, 2004.

* cited by examiner

*Primary Examiner* — Kimberly Chong
(74) *Attorney, Agent, or Firm* — Geoffrey M. Karny

(57) ABSTRACT

The present invention provides small interfering RNA (siRNA) molecules, compositions containing the molecules, and methods of using the molecules and compositions to treat breast cancer. In one aspect, a multi-targeted siRNAi cocktail is disclosed. The siRNA molecules may be encapsulated in nanoparticles to further enhance their anti-cancer activity. The compositions may also be used in combination with other anti-cancer agents, such as bevacizumab.

12 Claims, 17 Drawing Sheets

Fig 3.
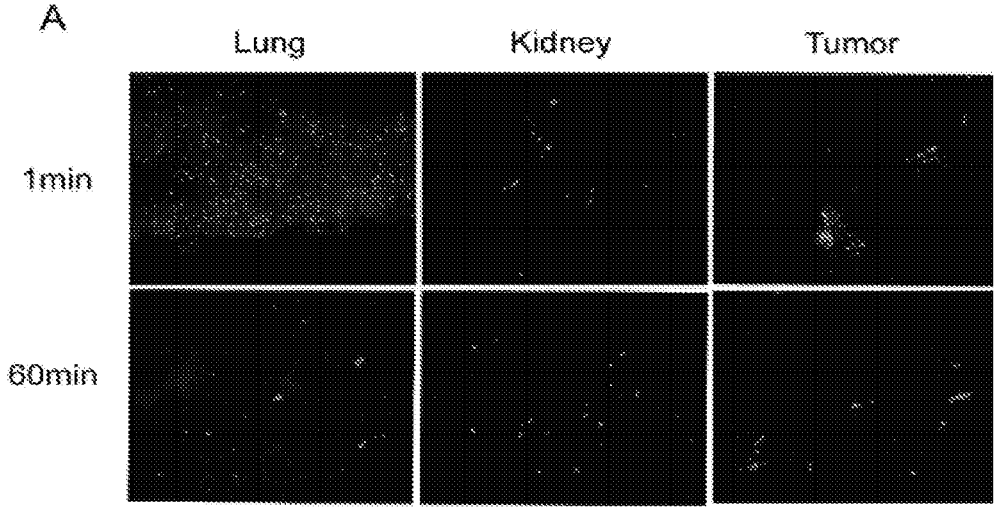
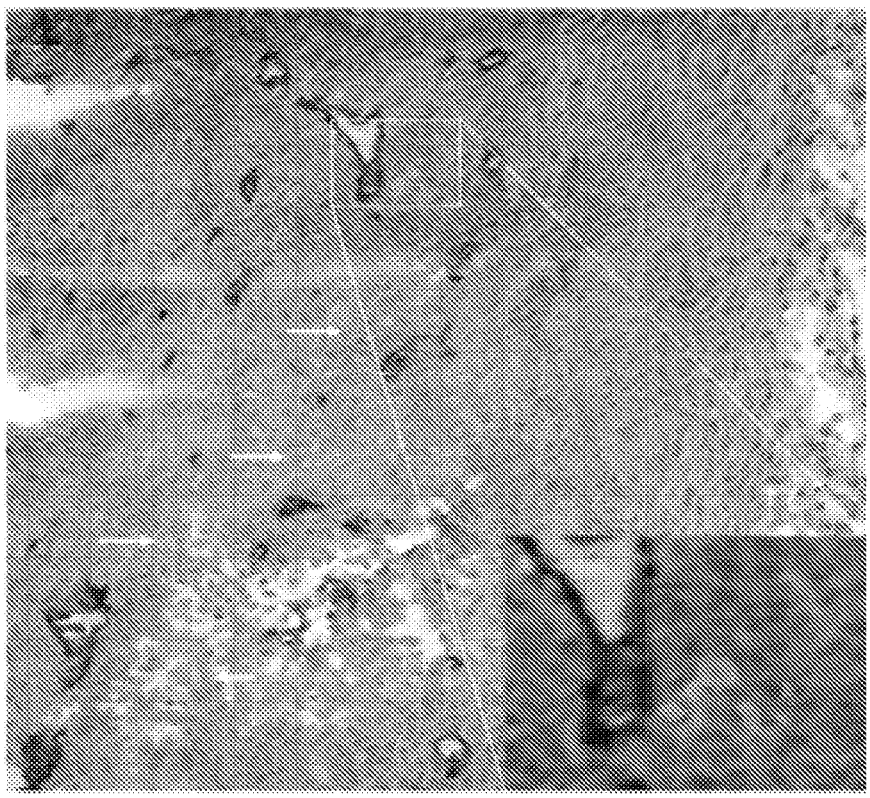

Fig 14. HKP Structure and HKP-siRNA Nanoparticles

COMPOSITIONS AND METHODS USING SIRNA MOLECULES AND SIRNA COCKTAILS FOR THE TREATMENT OF BREAST CANCER

This application is a U.S. national phase application of, and claims priority to and the benefit of, International Patent Application No. PCT/US2009/069950 filed Dec. 31, 2009, which claims priority to, and the benefit of, U.S. Provisional Patent Application No. 61/142,148, filed Dec. 31, 2008. The disclosures of these applications are expressly incorporated herein by reference in their entireties.

FIELD OF THE INVENTION

The invention relates to RNA interference and, in particular, the use of small interfering RNA (siRNA) molecules for the treatment of breast cancer.

BACKGROUND

According to CDC data, aside from non-melanoma skin cancer, breast cancer is the most common form of cancer in women. In fact, breast cancer is the number one cause of cancer death in Hispanic women, and it is also the second most common cause of cancer death across various ethnic groups in white, black, Asian/Pacific Islander, and American Indian/Alaska Native women. In 2004 (the most recent year numbers are available), 186,772 women and 1,815 men were diagnosed with breast cancer. The most common type of breast cancer, called ductal cancer, occurs in the cells of the breast ducts. Cancer that begins in the lobes or lobules is called lobular breast cancer. Lobular cancer is more often found in both breasts than other types of breast cancer. A third type of breast cancer, inflammatory breast cancer, is less common than the other two types.

The causative factors are not completely understood but are thought to be composed of both hereditary (e.g., BRCA1 and BRCA2 genes) and environmental (e.g., high fat diets, obesity, and smoking) factors. Despite multiple causative factors of breast cancer, the survival and growth of the breast cancer cells largely depend upon the common set of molecular signaling pathways in the cells.

Several molecular targets mediating interactive signal pathways have been implicated in the breast cancer formation and spread. Among these targets, EGFR, Raf-1 and mTOR are three prominent oncogenes in breast cancer promotion. Small molecule drugs and monoclonal antibodies have been developed or designed to block these targets with varying degrees of success. We believe that inhibition of these targets at the messenger RNA (mRNA) level will have a greater impact on the inhibition of breast cancer growth.

The Role of Epidermal Growth Factor Receptor in Breast Cancer

The epidermal growth factor receptor (EGFR) is the product of an activated oncogene. Elevated expression of EGFR is frequently detected in a wide variety of epithelial cell carcinomas, including breast, lung, head and neck, and cervical cancers, and it has been correlated with a poor prognosis. Agents that target members of the EGFR family have been approved for cancer therapy, such as ZD1839/Iressa and Herceptin.

The family of seven EGFR ligands includes EGF, TGFα, heparin-binding EGF-like growth factor (HB-EGF), amphiregulin (AR), betacellulin (BTC), epiregulin (EPR), and epigen. All of these ligands are synthesized as type-I transmembrane pro-ligands that consist of one or more EGF-like domains in their extracellular segments that are proteolytically cleaved to yield mature growth factors.

The EGFR signaling can also be transactivated by ligands of G-protein coupled receptors (GPCR). It was demonstrated that EGFRs were rapidly phosphorylated on the tyrosine residues after stimulation with the GPCR agonists, such as endothelin-1, lysophosphatidic acid or thrombin. The GPCR-EGFR cross-talk mechanism is now considered to be a widely interactive signal towards the activation of the MAP kinase pathway. EGFR transactivation is achieved by the action of many GPCRs and a variety of G-proteins.

The Gastrin-releasing peptide (GRP) binding to its receptor of GRPR has been shown to contribute to carcinogenesis by autocrine growth stimulation, resulting in acceleration of tumor cell proliferation. The importance of this pathway is underscored by the involvement of both autocrine growth pathways, TGF/EGFR and GRP/GRPR, in various types of cancers, including head and neck, lung, prostate, mammary, pancreas, colon, and ovary.

The Role of Raf-1 kinase in Breast Cancer

The Raf-1 kinase, a 72-kDa cytoplasmic serine-threonine kinase, plays a central role as a second messenger in signal transduction. After ligand binding to a variety of transmembrane tyrosine kinase growth factor receptors, including epidermal growth factor (EGF) receptor, the 72-kDa Raf-1 kinase is activated through phosphorylation by other cellular kinases to become a 74-kDa phosphoprotein.

The Raf-1 kinase is constitutively activated in many transformed cells either directly, by mutations within its amino-terminus regulatory region, or indirectly, due to overstimulation by autocrine growth factors or activated proximal oncogenes. Several human breast cancer cell lines have been reported to express varied amounts of EGF receptor to influence the level of Raf-1 protein expression as well as the proportion of Raf-1 expressed in the higher molecular weight form. Effects of serum starvation and stimulation with EGF on the Raf-1 protein were studied in T47D, BT474, and MDA-MB231 cells by immuno-precipitation. Raf-1 protein was pulled down from cell lysates with an anti-Raf-1 antibody for immunoblot analysis. [3H]Thymidine incorporation by these cells after EGF stimulation was also used as a measure of DNA synthesis, an indicator of cell cycle progression. In all three breast cancer cell lines studied, the Raf-1 protein was identified in a combination of 70-kDa and a 74-kDa forms. The level of Raf-1 was similar in all the three cell lines and appeared to be unrelated to EGF receptor expression on the cell surface. The majority of the protein was found in the 74-kDa form even after serum starvation. A minor shift from lower to higher molecular weight form of Raf-1 was apparent in cells treated with EGF, and increased [3H] thymidine incorporation could be demonstrated in two of the cell lines after EGF stimulation. Baseline expression of the 74-kDa or activated form of the Raf-1 kinase appeared to be elevated in the breast cancer cells studied, indicating constitutive activation.

Breast cancer disease progression may be characterized by a switch from hormone-dependent to hormone-independent growth that involves several cellular alterations and is a major problem in the treatment of breast cancer. Expression of a constitutively activated Raf in ER+ MCF-7 human breast cancer cells results in estrogen-independent growth, suggesting that activation of growth factor signaling pathways through Raf may confer a selective advantage for growth of breast cancer cells under estrogen-deprived conditions.

Raf-1 kinase inhibitor protein (RKIP) was originally identified as the first physiologic inhibitor of the Raf/mitogen-activated protein kinase kinase/extracellular signal-regulated kinase (ERK) pathway. This pathway regulates fundamental cellular functions, including those that are subverted in cancer cells, such as proliferation, transformation, survival, and metastasis. Recently, RKIP has been recognized as a strong candidate for a metastasis suppressor gene in cell and animal model systems. Clinical studies have indicated that that in human breast cancer, RKIP is a metastasis suppressor gene whose expression must be down-regulated for metastases to develop. RKIP expression is independent of other markers for breast cancer progression and prognosis. Therefore, inhibition of Raf-1 may contribute to control the metastases of breast cancer as well.

The Role of mTOR in Breast Cancer

The mammalian target of rapamycin (mTOR) is a serine-threonine kinase member of the phosphatidylinositol 3-kinase (PI3K) pathway, which is involved in multiple biologic functions, including transcriptional and translational control of downstream members' activities. mTOR is a downstream mediator in the PI3K/Akt signaling pathway and plays a critical role in cell survival. In breast cancer, this pathway can be activated by various membrane receptors, including the HER (or ErbB) family of growth factor receptors, the insulin-like growth factor receptor, and the estrogen receptor. There is evidence suggesting that Akt promotes breast cancer cell survival and resistance to chemotherapy, such as trastuzumab and tamoxifen.

Rapamycin is a specific mTOR antagonist that targets this pathway and blocks the downstream signaling elements, resulting in cell cycle arrest in the G1 phase. Targeting the Akt/PI3K pathway with mTOR antagonists may increase the therapeutic efficacy of breast cancer therapy.

Treatment of Breast Cancer

There are different types of treatment for patients with breast cancers. Four major methods of standard treatment of breast cancers are surgery, radiation therapy, chemotherapy, and hormone therapy. New types of treatment are also being tested in clinical trials now. These include the following: sentinel lymph node biopsy followed by surgery, high-dose chemotherapy with stem cell transplant, monoclonal antibodies as adjuvant therapy, and tyrosine kinase inhibitors as adjuvant therapy.

When discovered early, breast cancer can be treated with the above-mentioned therapies with a high rate of survival. The 5-year survival rate is now reaching over 70%, and the 10-year survival rate is about 50%. However, once the cancer spreads out to other tissues or organs, the survival rate with any of the treatments falls dramatically. Treatment of breast cancer depends on the types of cancers with varying degrees of success. Despite the recent integration of more powerful endocrine agents into breast cancer care, resistance to all forms of endocrine therapy remains a major problem. Therefore, more effective new therapies are absolutely needed.

An attractive approach for therapeutic intervention would be to inhibit all the targets along the pathways of EGFR, Raf-1 and mTOR, which all contribute to breast cancer growth. The three genes have been shown individually to be involved in the development of breast cancer. We hypothesized that a new, more effective therapeutic approach would be to suppress all three oncogenes simultaneously and preferably in combination with different anti-cancer agents.

Gene Inhibition by siRNA as an Alternative Therapeutic

Major advances in molecular biology, cellular biology and genomics have greatly enhanced our knowledge about gene regulation mechanisms in cancers. Gene silencing methods, such as antisense and ribozymes, have been shown to down-regulate disease related genes. Novel technologies, such as siRNA, have been developed and tested to show the safety and effectiveness of disease treatment, including but not limited to cancers, in many animal models.

RNA interference (RNAi) is a sequence-specific RNA degradation process that provides a relatively easy and direct way to knockdown, or silence, theoretically any gene containing the homologous sequence. In naturally occurring RNAi, a double-stranded RNA (dsRNA) is cleaved by an RNase III/helicase protein, Dicer, into small interfering RNA (siRNA) molecules, dsRNA of 19-27 nucleotides (nt) with 2-nt overhangs at the 3' ends. Afterwards, the siRNAs are incorporated into a multicomponent-ribonuclease called RNA-induced-silencing-complex (RISC). One strand of siRNA remains associated with RISC to guide the complex towards a cognate RNA that has a sequence complementary to the guider ss-siRNA in RISC. This siRNA-directed endonuclease digests the RNA, resulting in truncation and inactivation of the targeted RNA. Recent studies have revealed the utility of chemically synthesized 21-27-nt siRNAs that exhibit RNAi effects in mammalian cells and have demonstrated that the thermodynamic stability of siRNA hybridization (at terminals or in the middle) plays a central role in determining the molecule's function. More detailed characteristics of RISC, siRNA molecules, and RNAi have been described in the scientific literature.

The utility of RNAi in down-regulation of mammalian cell gene expression has been shown successfully in the laboratory by utilizing either chemically synthesized siRNAs or endogenously expressed siRNA. The endogenous siRNA is first expressed as small hairpin RNAs (shRNAs) by an expression vector (plasmid or virus vector), and then processed by Dicer to become functional siRNAs.

Importantly, it is presently not possible to predict with any degree of confidence which of many possible candidate siRNA sequences potentially targeting a genomic sequence (e.g., oligonucleotides of about 16-30 base pairs) will in fact exhibit effective siRNA activity. Instead, individual, specific candidate siRNA polynucleotide or oligonucleotide sequences must be generated and tested to determine whether the intended interference with expression of a targeted gene has occurred. Accordingly, no routine method exists for designing an siRNA polynucleotide that is, with certainty, capable of specifically altering the expression of a given mRNA. Our process involves design of multiple siRNA sequences against a single gene and then testing of these sequences to validate their potency at silencing the selected gene as well as their selectivity (specificity for the target gene and not others).

SUMMARY OF THE INVENTION

The present invention provides an isolated small interfering RNA (siRNA) molecule that binds to a single-stranded RNA molecule, wherein the single-stranded RNA molecule comprises an mRNA that encodes at least part of a peptide or protein whose activity promotes tumorigenesis, angiogenesis, cell proliferation, or anti-apoptosis in the breast tissue of a mammal, or wherein the single stranded RNA molecule comprises an miRNA whose activity promotes tumorigenesis, angiogenesis, cell proliferation, or anti-apoptosis in the breast tissue of a mammal.

The invention further provides compositions comprising one or more of the siRNA molecules in a pharmaceutically acceptable carrier. In one embodiment, the invention provides a composition comprising at least three of the siRNA molecules in a pharmaceutically acceptable carrier. In a particular embodiment, the molecules bind to multiple, different target sequences in the single-stranded RNA molecule or in different single stranded RNA molecules. In one embodiment, the carrier comprises at least one of the following: a glucose solution, a polycationic binding agent, a cationic lipid, a cationic micelle, a cationic polypeptide, a hydrophilic polymer grafted polymer, a non-natural cationic polymer, a cationic polyacetal, a hydrophilic polymer grafted polyacetal, a ligand functionalized cationic polymer, a ligand functionalized-hydrophilic polymer grafted polymer, and a ligand functionalized liposome.

These compositions may include, or be used with, another therapeutic agent that impedes or blocks tumorigenesis, angiogenesis, cell proliferation, or anti-apoptosis in the breast of a mammal.

The invention also provides a method for treating breast cancer in a subject comprising administering to the subject a therapeutically effective amount of a composition of the invention. In one embodiment, the subject is a human.

The invention also provides a nanoparticle comprising the siRNA molecule of the invention, a carrier, and a targeting ligand. In one embodiment, the nanoparticle comprises three different siRNA molecules, a carrier, and a targeting ligand.

BRIEF DESCRIPTION OF THE FIGURES

FIG. 3. Accumulation of intravenously (IV) delivered HKP-encapsulated siRNA molecules in established head and neck squamous cancer 1483 xenograft tumors. A: Images of mouse tissues and tumors with Alexa Fluor 555 labeled fluorescent siRNA CT-2 deposits following tail vein injection of HKP-siRNA. The tissues were harvested at the indicated time, freshly frozen, sectioned, and analyzed by fluorescent microscopy. Magnification: 400×. B: Accumulation of fluorescent CT-2 (Red deposits indicated with arrows) in the tumors in proximity to blood vessels (Brown; CD31 immunostaining) Magnification: 400×. Inset: Detail showing siRNA.

DETAILED DESCRIPTION OF THE INVENTION

Figure 1:
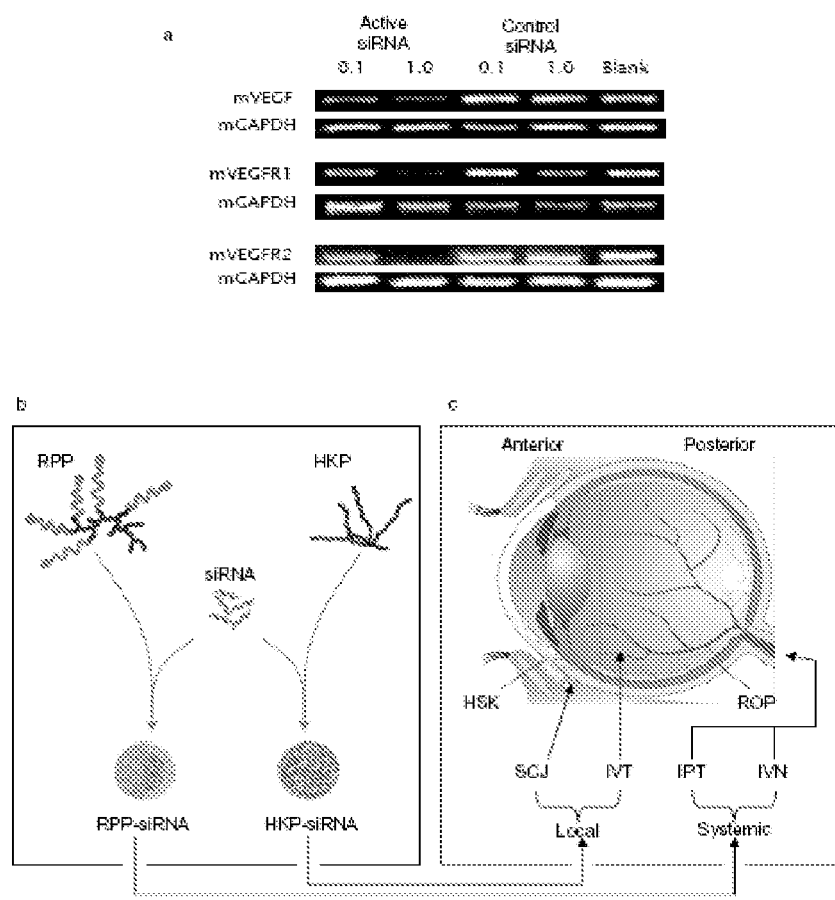
FIG. 1. Demonstration of the efficacy of polymer-siRNA nanoparticles targeted to three individual mouse genes, VEGF, VEGFR1 and VEGFR2. Polymer-siRNA nanoparticles (a) RT-PCR analyses for mRNA levels of mVEGF, mVEGFR1 and mVEGFR2. Two dosages of the siRNA oligos were used against the same dosage of control siRNA oligos. (b) Formations of two different types of polymeric siRNA nanoparticles. HKP-siRNA particles can be formed when HKP aqueous solution mixed with siRNA solution, and so do the RPP-siRNA particles. (c) siRNA oligos were delivered through both local and systemic administrations. Two murine ocular NV models, HSK representing corneal disease and ROP representing retinopathy disease, were applied respectively. HKP-siRNA particles were mainly for local deliveries through either subconjunctival (SCJ) or intravitreous (IVT) route. RPP-siRNA particles were applied for systemic deliveries through either intraperitoneal (IPT) or intravenous (IVN) routes, respectively, reaching to the blood stream first and then to ocular neovasculature.

The invention provides siRNA molecules, compositions containing the molecules, and methods of using the molecules and compositions to treat breast cancer (breast carcinoma) in a mammal, such as a human patient. As used herein, an "siRNA molecule" is a duplex oligonucleotide, that is a short, double-stranded oligonucleotide, that interferes with the activity of RNA expressed by a gene in a cell, after the molecule is introduced into the cell. Such molecules are constructed by techniques known to those skilled in the art. Such techniques are described in U.S. Pat. Nos. 5,898,031, 6,107, 094, 6,506,559, 7,056,704 and in European Pat. Nos. 1214945 and 1230375, which are incorporated herein by reference in their entireties.

The siRNA molecule of the invention is an isolated siRNA molecule that binds to a single stranded RNA molecule, which is a messenger RNA (mRNA) that encodes at least part of a peptide or protein whose activity promotes tumorigenesis, angiogenesis, cell proliferation, or anti-apoptosis in the breast tissue of a mammal, or which is a micro-RNA (miRNA) whose activity promotes tumorigenesis, angiogenesis, cell proliferation, or anti-apoptosis in the breast tissue of a mammal. Such activity can cause or promote the growth of breast cancer or cause or promote its metastasis. In one embodiment, the molecule is an oligonucleotide with a length of about 19 to about 35 base pairs. In another embodiment, the molecule is an oligonucleotide with a length of about 19 to about 27 base pairs. In still another embodiment, the molecule is an oligonucleotide with a length of about 21 to about 25 base pairs. In all of these embodiments, the molecule may have blunt ends at both ends, or sticky ends at both ends, or a blunt end at one end and a sticky end at the other. In one particular embodiment, it has blunt ends at both ends.

The siRNA molecule can be made of naturally occurring ribonucleotides, i.e., those found in living cells, or one or more of its nucleotides can be chemically modified by techniques known in the art. In addition to being modified at the level of one or more of its individual nucleotides, the backbone of the oligonucleotide also can be modified. Additional modifications include the use of small molecules (e.g. sugar molecules), amino acid molecules, peptides, cholesterol and other large molecules for conjugation onto the siRNA molecules. Such modifications can protect the molecule from degradation, improve its potency, reduce its toxicity, and reduce its immune stimulatory effect.

The siRNA molecule may further comprise an immune stimulatory motif Such motifs can include specific RNA sequences such as 5'-UGUGU-3' (Judge et al., *Nature Biotechnology* 23, 457-462 (1 Apr. 2005)), 5'-GUCCUUCAA-3' (Hornung et al., *Nat. Med.* 11, 263-270(2005). See Kim et al., *Mol Cell* 24; 247-254 (2007). These articles are incorporated herein by reference in their entireties. These are siRNA sequences that specifically activate immune responses through Toll-like receptor (TLR) activation or through activation of key genes such as RIG-I or PKR. In one embodiment, the motif induces a TH1 pathway immune response. In another embodiment, the motif comprises 5'-UGUGU-3',5'-GUCCUUCAA-3',5'-GGGxGG-3' (where x is A, T, G and C), or CpG motifs 5'-GTCGTT-3'.

In one embodiment, the siRNA molecule binds to an mRNA that encodes at least part of a peptide or protein whose activity promotes tumorigenesis, angiogenesis, cell proliferation, or anti-apoptosis in the breast tissue of a mammal. Such may be the case when the mRNA molecule encodes a protein in a pro-tumorigenic pathway, pro-angiogenesis pathway, pro-cell proliferation pathway, or anti-apoptotic pathway. For example, the protein can be an EGFR pathway protein, Raf-1 pathway protein, mTOR pathway protein, VEGF pathway protein, HIF-1 alpha pathway protein, Her-2 pathway protein, MMP pathway protein, PDGF pathway protein, or Cox-2 pathway protein. In one embodiment, the protein is one of the following: EGFR, Raf-1, mTOR, VEGF, HIF-1 alpha, Her-2, MMP-9, PDGF, or Cox-2. In a particular embodiment, the protein is EGFR, Raf-1, or mTOR. In another particular embodiment, the protein is EGFR, VEGF, or MMP-9. In another particular embodiment, the protein is EGFR, VEGF, or Cox-2. In another particular embodiment, the protein is EGFR, VEGF, or PDGF. In another particular embodiment, the protein is EGFR, Raf-1, or PDGF. Particular target sequences are shown in Tables 1-6 herein. Thus, certain particular siRNA molecules of the invention bind to and inhibit expression of one or more of the sequences identified in these tables.

In one embodiment, the siRNA molecule binds to both a human mRNA molecule and a homologous mouse mRNA molecule. That is, the human and mouse mRNA molecules encode proteins that are substantially the same in structure or function. Therefore, the efficacy and toxicity reactions observed in the mouse disease models (e.g. xenograft tumor models) will allow us to have a good understanding about what is going to happen in humans. Moreover, the siRNA molecules tested in the mouse model are good candidates for human pharmaceutical agents. The human/mouse homology design of an siRNA drug agent can eliminate the toxicity and adverse effect of those species specificities observed in monoclonal antibody drugs.

In another embodiment, the siRNA molecule binds to an miRNA whose activity promotes tumorigenesis, angiogenesis, cell proliferation, or anti-apoptosis in the breast tissue of a mammal. As used herein, an miRNA is a short, single-stranded RNA molecule that down-regulates gene expression through a loose homology binding to the 3' end of the untranslated region of a particular gene target. Such molecules are transcribed from DNA, but are not translated into a polypeptide.

Similarly, siRNA molecules can be designed to bind to other single-stranded RNA molecules that can regulate gene expression through mechanisms other than the RNAi effect.

The siRNA molecules of the invention kill breast cancer cells. An effective amount of the molecules, i.e., an amount that directly or indirectly kills one or more of the cells, is administered to the cells by techniques known to those skilled in the art. Thus, the molecules are used to treat breast cancer in a mammal, particularly a human. A plurality of the molecules are used. The siRNA molecules may bind to an mRNA that encodes a peptide or protein that causes or promotes the growth of breast cancer or causes or promotes its metastasis, or it may bind to an miRNA whose activity causes or promotes the growth of breast cancer or causes or promotes its metastasis. In one embodiment, the mammal is a human, non-human primate, or rodent, such as a mouse, rat, or guinea pig. Rodents are particularly useful for laboratory experiments with the molecules. In a particular embodiment, the mammal is a human. The molecules are delivered to the subject in pharmaceutically acceptable carriers known to those skilled in the art by techniques known to those skilled in the art.

The invention also includes compositions of one or more of the siRNA molecules. Where there is a plurality of different siRNA molecules, each one targets a different RNA nucleotide sequence, which can be on the same RNA target molecule, different RNA target molecules, or any combination thereof. These compositions, by themselves or in combination with pharmaceutically acceptable carriers such as those described herein, are sometimes called siRNA cocktails. Thus, the invention provides multi-targeted siRNA cocktails for the treatment of breast cancer.

All possible combinations of types of molecules and targets are included in the invention. For example, the targeted RNA molecules may encode or regulate the expression of one or more proteins in the mammal. The targeted RNA molecules include mRNA and/or miRNA as described above. The proteins can be in the same or different pathways. The pathways, categories of proteins, and specific proteins are the ones identified herein. In one embodiment, the composition comprises two or more different siRNA molecules, each binding to a different RNA target sequence. In another embodiment, the composition comprises three different siRNA molecules, each binding to a different RNA target sequence. In still another embodiment, the composition comprises more than three different siRNA molecules, each binding to a different RNA target sequence. In one embodiment, the siRNA molecules target one or more of the mRNA sequences that are transcribed from one or more of the gene sequences listed in Tables 1-6 herein.

In yet another embodiment, the composition comprises at least one siRNA molecule (sense: 5'-CUGUAGACACAC-CCACCCACAUACA-3', antisense: 5'-UGUAU-GUGGGUGGGUGUGUCUACAG-3') that binds to an mRNA molecule that encodes human VEGF protein and to an mRNA molecule that encodes mouse VEGF protein, at least one siRNA molecule (sense: 5'-CCAUCGAUGUCUA-CAUGAUCAUGGU-3', antisense: 5'-ACCAUGAUCAU-GUAGACAUCGAUGG-3') that binds to an mRNA molecule that encodes human EGFR protein and to an mRNA molecule that encodes mouse EGFR protein, and at least one siRNA molecule (sense: 5'-GGUCUGGUGCCUGGU-CUGAUGAUGU-3', antisense: 5'-ACAUCAUCAGAC-CAGGCACCAGACC-3'-3') that binds to an mRNA molecule that encodes human Cox-2 protein and to an mRNA molecule that encodes mouse Cox-2 protein.

As previously mentioned, the siRNA cocktails of the invention comprise two or more different siRNA molecules of the invention in a pharmaceutically acceptable carrier. Such carriers are generally known to those skilled in the art and include saline, sugars, polypeptides, polymers, lipids, creams, gels, micelle materials, and metal nanoparticles. In one embodiment, the carrier comprises at least one of the following: a glucose solution, a polycationic binding agent, a cationic lipid, a cationic micelle, a cationic polypeptide, a hydrophilic polymer grafted polymer, a non-natural cationic polymer, a cationic polyacetal, a hydrophilic polymer grafted polyacetal, a ligand functionalized cationic polymer, a ligand functionalized-hydrophilic polymer grafted polymer, and a ligand functionalized liposome. In another embodiment, the polymers comprise a biodegradable histidine-lysine polymer, a biodegradable polyester, such as poly(lactic acid) (PLA), poly(glycolic acid) (PGA), and poly(lactic-co-glycolic acid)

(PLGA), a polyamidoamine (PAMAM) dendrimer, a cationic lipid, or a PEGylated PEI. Cationic lipids include DOTAP, DOPE, DC-Chol/DOPE, DOTMA, and DOTMA/DOPE. In still another embodiment, the carrier is a histidine-lysine copolymer that forms a nanoparticle with the siRNA molecule, wherein the diameter of the nanoparticle is about 100 nm to about 400 nm. In a further embodiment, the ligand comprises one or more of an RGD peptide, such as H-ACRGDMFGCA-OH, an RVG peptide, such as H-YTIW-MPENPRPGTPCDIFTNSRGKRASNG-OH, or a FROP peptide, such as H-EDYELMDLLAYL-OH.

The invention also provides a nanoparticle comprising one or more of the siRNA molecules of the invention, a carrier, such as one or more of those described herein, and a targeting ligand. In one particular embodiment, the diameter of the nanoparticle is about 100 nm to about 400 nm. Examples of targeting ligands include EGF receptor ligands, IL13 ligand, hepatocyte growth factor ligand, single chain monoclonal antibodies, RGD peptide ligands, and RVG peptide ligands. In one embodiment, the nanoparticle comprises an RGD peptide ligand. Such ligands include a 'cyclic' 10 mer RGD peptide with the sequence H-ACRGDMFGCA-OH, and -(D)CR(D)WKTCT-(ol). In another embodiment, it comprises an RVG peptide ligand. Such ligands include YTIWMPEN-PRPGTPCDIFTNSRGKRASNG or YTIWMPENPRPGT-PCDIFTNS-RGKRASNGGGGRRRRRRRRR.

These nanoparticles may be used to prepare the siRNA cocktails previously described herein. Thus, the invention also includes a composition comprising 3 or more of the nanoparticles described herein.

The invention also provides a method of treating a mammal with a breast cancer by administering to the mammal a therapeutically effective amount of one or more of the siRNA molecules of the invention or a therapeutically effective amount of one or more of the compositions of the invention. In one embodiment, the mammal is a human, non-human primate or rodent. In a particular embodiment, the mammal is a human patient. The breast cancer may be characterized at least in part by neovascularization and inflammation in the mammal's breast tissue.

The compositions are administered by techniques known to those skilled in the art. In one embodiment, the composition comprises at least three siRNA molecules at a ratio determined by the potency of each siRNA molecule and the therapeutic needs of the mammal. In another embodiment, the composition comprises three different siRNA molecules at a ratio of 1:1:1, 1:1.5:0.5, or 0.5:0.5:2.

The compositions of the invention can be used with a therapeutically effective amount of other anti-cancer agents. These include ones that impede or block tumorigenesis, angiogenesis, cell proliferation, or anti-apoptosis in the breast tissue of a mammal. In one embodiment, the agent impedes or blocks the activity of a peptide or protein whose activity promotes tumorigenesis, angiogenesis, cell proliferation, or anti-apoptosis in the breast tissue of the mammal. For example, it may impede or block the activity of a peptide or protein that causes or promotes the growth of a breast cancer or causes or promotes its metastasis. In one embodiment, it impedes or blocks the activity of a protein that is a pro-tumorigenic pathway protein, a pro-angiogenesis pathway protein, a pro-cell proliferation pathway protein, or an anti-apoptotic pathway protein. Such proteins include, but are not limited to, an EGFR pathway protein, Raf-1 pathway protein, mTOR pathway protein, VEGF pathway protein, HIF-1 alpha pathway protein, Her-2 pathway protein, MMP pathway protein, PDGF pathway protein, or Cox-2 pathway protein. Particular examples of proteins that may be targeted by the therapeutic agent are: EGFR, Raf-1, mTOR, VEGF, HIF-1 alpha, Her-2, MMP-9, PDGF, or Cox-2. In one embodiment, the protein is EGFR, Raf-1, or mTOR. In another embodiment, the protein is EGFR, VEGF, or MMP-9. In another embodiment, the protein is EGFR, VEGF, or Cox-2. In another embodiment, the protein is EGFR, VEGF, or PDGF. In another embodiment, the protein is EGFR, Raf-1, or PDGF.

In one embodiment of the invention, the therapeutic agent is selected from the group consisting of bevacizumab (trade name Avastin), sunitinib (trade name Sutent), sorafenib (trade name Nexavar), temsirolimus (trade name Torisel), and temozolomide (trade name Temodar). In a particular embodiment, the agent is bevacizumab. In another particular embodiment, the composition of the invention comprises bevacizumab and siRNA molecules that inhibit the expression of one or more of the following: EGFR, Raf-1, and mTOR. In still another particular embodiment, a composition comprises bevacizumab and siRNA molecules that inhibit the expression of EGFR, Raf-1, and mTOR.

EXAMPLES

The following examples illustrate certain aspects and embodiments of the invention and should not be construed as limiting the scope thereof.

Overview

The present invention relates to multi-targeted RNA interference (RNAi) cocktails for treatment of cancers, particularly breast cancers. In the preliminary studies, we have demonstrated that EGFR and Raf-1 were essential for breast cancer cell growth. Literature suggests that mTOR is another key player involved in the breast cancer development and would be a valid target for siRNA-mediated therapeutics.

To ensure the potency of each siRNA duplex for the target gene knockdown, there are several features that should be considered during the in silico design and the later in vitro and in vivo tests: (1) to have the optimum thermodynamics for target sequence binding, (2) to have sufficient length for RISC binding, (3) to eliminate immune stimulation motifs, (4) to have human-mouse homology, (5) to avoid "off-target" potential through BLAST searches and (6) to be able to form a multi-targeted siRNA cocktail.

In one embodiment, we will design siRNA duplexes targeting to the conserved gene sequences shared by both mouse and human. This approach will ensure that, when an siRNA duplex is used in a mouse xenograft tumor model, both human and mouse corresponding genes are silenced. As a result, the siRNA drug being selected is able to avoid the species specificity issue and cytokine cross-reactivity issue. In addition, our preliminary results have demonstrated that a 25 mer siRNA is more potent than a 21 mer siRNA due to the reasons described above. We have therefore used 25 mer siRNAs in our multi-targeted siRNA cocktail targeting EGFR, Raf-1 and mTOR genes simultaneously. The gene silencing potencies will be tested and validated first in the cell culture experiments by RT-PCR and ELISA for efficacy of multi-targeting siRNA on gene knockdown at both transcription and translation levels. Other cell-based phenotypic changes (like apoptosis) will also be examined (with TUNNEL assay) as reassuring references to possible variations among cell lines. Once the most effective siRNA duplexes are selected for EGFR, Raf-1 and mTOR from the gene knockdown experiments in cell culture models, we will further investigate the optimal combination of siRNA set as the active pharmaceutical ingredient (API) and tested optimized siRNA combinations in the mouse model.

The siRNAs are to be in silico designed according certain considerations described above. We have developed an algorithm that is able to search published intellectual property databases and identify siRNA duplexes having (1) optimum thermodynamics, (2) enhanced RISC binding, (3) eliminated immune stimulation motifs, (4) human-mouse homology, (5) minimized "off-target" potential, and (6) different lengths at 21, 23, 25 and 27 mer, etc. Using this web-based algorithm, we are able to identify siRNA sequences targeted to specific genes. The targeted sequences within the genes EGFR, Raf-1, mTOR, VEGF, HIF-1alpha, and Her-2 are listed in the following tables.

TABLE 1

Sequence templates used in the design of EGFR targeted siRNA duplexes

| Gene homology | Length | No. | Sense Sequences |
|---|---|---|---|
| EGFR Human (NM_005228) Mouse (AF275367) | 21-mer | 1 | cccugacuaccagcaggacuu |
| | | 2 | cugacuaccagcaggacuucu |
| | | 3 | caggggggaugaaagaaugcau |
| | | 4 | gggggaugaaagaaugcauuu |
| | | 5 | gaauucuccaaaauggcccga |
| | | 6 | ccaucgaugucuacaugauca |
| | | 7 | gaucauggucaagugcuggau |
| | | 8 | cgaugucuacaugaucauggu |
| | | 9 | caaagugccuaucaaguggau |
| | | 10 | cuggaucccagaaggugagaa |
| | 23-mer | 1 | gacaacccugacuaccagcagga |
| | | 2 | caacccugacuaccagcaggacu |
| | | 3 | cccugacuaccagcaggacuucu |
| | | 4 | caggggggaugaaagaaugcauuu |
| | | 5 | ggaugaaagaaugcauuugccaa |
| | | 6 | gaauucuccaaaauggcccgaga |
| | | 7 | cgaugucuacaugaucaugguca |
| | | 8 | cuacaugaucauggucaagugcu |
| | | 9 | ggcaaagugccuaucaaguggau |
| | | 10 | cucuggaucccagaaggugagaa |
| | 25-mer | 1 | 5'-gacaacccugacuaccagcaggacu-3' |
| | | 2 | 5'-ggggaugaaagaaugcauuugccaa-3' |
| | | 3 | 5'-gacaacccugacuaccagcaggacu-3' |
| | | 4 | 5'-ggggaugaaagaaugcauuugccaa-3' |
| | | 5 | 5'-ccaucgaugucuacaugaucauggu-3' |
| | | 6 | 5'-gaugucuacaugaucauggucaagu-3' |
| | | 7 | 5'-gucuacaugaucauggucaagugcu-3' |
| | | 8 | 5'-gaucauggucaagugcuggaugaua-3' |
| | | 9 | 5'-gaucacagauuuugggcuggccaaa-3' |
| | | 10 | 5'-cagauuugggcuggccaaacugcu-3' |

TABLE 2

Sequence templates used in the design of Raf-1 targeted siRNA duplexes

| Gene homology | Length | No. | Sense Sequences |
|---|---|---|---|
| A-RAF Human (NM_001654) Mouse (NM_009703) | 21-mer | 1 | ggcccugaaggugcgggucu |
| | | 2 | cacugccugggacacagccau |
| | | 3 | cugaccaugcacaauuuugua |
| | | 4 | ccaugcacaauuuuguacgga |
| | | 5 | caugcacaauuuuguacggaa |
| | | 6 | cugugacuucugccuuaaguu |
| | | 7 | cugccuuaaguuucuguucca |
| | | 8 | ggaagucccacauuccaagu |
| | | 9 | gaggaagucccacauuccaa |
| | | 10 | gauccguaugcaggacccgaa |
| | 23-mer | 1 | gucacugccugggacacagccau |
| | | 2 | gaccaugcacaauuuuguacgga |
| | | 3 | caugcacaauuuuguacggaaga |
| | | 4 | guggcuacaaguuccaccagcau |
| | | 5 | cuacaaguuccaccagcauuguu |
| | | 6 | caaguuccaccagcauuguuccu |
| | | | caccagcauuguuccuccaaggu |
| | | 8 | gaggaagucccacauuccaagu |
| | | 9 | ccuggggguaccgggacucaggcu |
| | | 10 | ggugauccguaugcaggacccga |
| | 25-mer | 1 | 5'-cugaccaugcacaauuuuguacgga-3' |
| | | 2 | 5'-ccuguggcuacaaguuccaccagca-3' |

TABLE 2-continued

Sequence templates used in the design of Raf-1 targeted siRNA duplexes

| Gene homology | Length | No. | Sense Sequences |
|---|---|---|---|
| | | 3 | 5'-cugaccaugcacaauuuuguacgga-3' |
| | | 4 | 5'-ggcuacaaguuccaccagcauuguu-3' |
| | | 5 | 5'-ccuguggcuacaaguuccaccagca-3' |
| | | 6 | 5'-gggaggaagucccacauuccaagu-3' |
| | | 7 | 5'-gugaagaaccuggguaccgggacu-3' |
| | | 8 | 5'-cagcauuguuccuccaagguccca-3' |
| | | 9 | 5'-ccuggguaccgggacucaggcuau=3 |
| | | 10 | 5'-gaggugauccguaugcaggacccga-3' |

TABLE 3

Sequence templates used in the design of mTOR targeted siRNA duplexes

| Gene homology | | Length | No. | Sense Sequences |
|---|---|---|---|---|
| mTOR | Human (L34075) | 21-mer | 1 | gccgaagccgcgcgaaccuca |
| | Mouse (AF152838) | | 2 | gccgcgcgaaccucagggcaa |
| | | | 3 | gaggagucuacucgcuucuau |
| | | | 4 | gguuccagcucagaugccaa |
| | | | 5 | gcucagaugccaaugagagga |
| | | | 6 | cagcauggagggagagcgucu |
| | | | 7 | ggugugccagugggugcugaa |
| | | | 8 | ggguccuuugugaagagcca |
| | | | 9 | ccagcuguuggcgccaaccu |
| | | | 10 | gccagggaucucuucaaugcu |
| | | 23-mer | 1 | gccgcgcgaaccucagggcaaga |
| | | | 2 | gaggagucuacucgcuucuauga |
| | | | 3 | guuuccagcucagaugccaauga |
| | | | 4 | cagcucagaugccaaugagagga |
| | | | 5 | cagcauggagggagagcgucuga |
| | | | 6 | caggccaucaccuucaucuucaa |
| | | | 7 | ggguccuuugugaagagccaca |
| | | | 8 | cacuacaaagaacuggaguucca |
| | | | 9 | gccaugaaacacuuuggagagcu |
| | | | 10 | gagguuauccaguacaaacuugu |
| | | 25-mer | 1 | 5'-gcgcgaaccucagggcaagaugcuu-3' |
| | | | 2 | 5'-guuuccagcucagaugccaaugaga-3' |
| | | | 3 | 5'-cagcauggagggagagcgucugaga-3' |
| | | | 4 | 5'-caggccaucaccuucaucuucaagu-3' |
| | | | 5 | 5'-ccagcuguuuggcgccaaccuggau-3' |
| | | | 6 | 5'-cacuacaaagaacuggaguuccaga-3' |
| | | | 7 | 5'-gccaugguuucuugccacaugcugu-3' |
| | | | 8 | 5'-ggucccuugugguucagcccucauga-3' |
| | | | 9 | 5'-cugcgucaugccagcggggccaaca-3' |
| | | | 10 | 5'-gguuugauuauggucacuggccaga-3' |

TABLE 4

Sequence templates used in the design of VEGF targeted siRNA duplexes

| Gene | homology | Length | No. | Sense Sequences |
|---|---|---|---|---|
| VEGF165 | Human | 21-mer | 1 | gugugcgcagacagugcucca |
| | (NM_001025366) | | 2 | ccaccaugccaagugguccca |
| | Mouse | | 3 | ccugguggacaucuuccagga |
| | (NM_001025250) | | 4 | gcacauaggagagaugagcuu |
| | | | 5 | caagauccgcagacguguaaa |
| | | | 6 | ggcgaggcagcuugaguuaaa |
| | | | 7 | cuugaguuaaaacgaacguacu |
| | | | 8 | ggaaggagccucccucagggu |
| | | | 9 | cacuuugggguccggagggcga |
| | | | 10 | caguauucuugguuaauauuu |
| | | 23-mer | 1 | gccuccgaaaccaugaacuuucu |
| | | | 2 | cuccaccaugccaaguggucccca |

TABLE 4-continued

Sequence templates used in the design of VEGF targeted siRNA duplexes

| Gene | homology | Length | No. | Sense Sequences |
|---|---|---|---|---|
| | | | 3 | ccuggug gacaucuuccaggagu |
| | | | 4 | cagcacauaggagaugagcuu |
| | | | 5 | gcuugaguuaaacgaacguacuu |
| | | | 6 | guuaaacgaacguacuugcagau |
| | | | 7 | ggaaggagccucccucagggguu |
| | | | 8 | cucccucaggguuucgggaacca |
| | | | 9 | cuaauguuauuggugucuucacu |
| | | | 10 | gagaaaguguuuuauauacggua |
| | | 25-mer | 1 | 5'-ccuccgaaaccaugaacuuucugcu-3' |
| | | | 2 | 5'-ccaccaugccaaguggucccaggcu-3' |
| | | | 3 | 5'-cccuggug gacaucuuccaggagua-3' |
| | | | 4 | 5'-gauccgcagacguguaaauguuccu-3' |
| | | | 5 | 5'-cgcagacguguaaauguuccugcaa-3' |
| | | | 6 | 5'-guaaauguuccugcaaaaacacaga-3' |
| | | | 7 | 5'-cagcuugaguuaaacgaacguacuu-3' |
| | | | 8 | 5'-guuaaacgaacguacuugcagaugu-3' |
| | | | 9 | 5'-ccaugccaaguggucccaggcugca-3' |
| | | | 10 | 5'-cccuggug gacaucuuccaggagua-3' |

TABLE 5

Sequence templates used in the design of HIF-1 alpha targeted siRNA duplexes

| Gene | homology | Length | No. | Sense Sequences |
|---|---|---|---|---|
| HIF-1 alpha | Human (NM_001530) Mouse (NM_010431) | 21-mer | 1 | guucugaacgucgaaaagaaa |
| | | | 2 | gaaguuuuuaugagcuugcu |
| | | | 3 | gagcuugcucaucaguugcca |
| | | | 4 | caguacaggaugcuugccaaa |
| | | | 5 | gcucccuauaucccaauggau |
| | | | 6 | cuggacacagugug uuugauu |
| | | | 7 | cacaguguguuugauuuuacu |
| | | | 8 | guggauuaccacagcugacca |
| | | | 9 | cagaaaccuacugcagggguga |
| | | | 10 | ggugaagaauuacucagagcu |
| | | 23-mer | 1 | cugaacgucgaaaagaaaagucu |
| | | | 2 | gaaguuuuuaugagcuugcuca |
| | | | 3 | gagcuugcucaucaguugccacu |
| | | | 4 | gacaguacaggaugcuugccaaa |
| | | | 5 | gaacuaacuggacacagugug uu |
| | | | 6 | cacagug uuugauuuuacuca |
| | | | 7 | gacacaguguguuugauuuuacu |
| | | | 8 | cucauccaugugaccaugaggaa |
| | | | 9 | gaccaugaggaaaugagagaaau |
| | | | 10 | gagaaaugcuuacacacagaaau |
| | | 25-mer | 1 | 5'-guuuuuaugagcuugcucaucagu-3' |
| | | | 2 | 5'-gacacagugug uuugauuuuacuca-3' |
| | | | 3 | 5'-caggacaguacaggaugcuugccaa-3' |
| | | | 4 | 5'-cucauccaugugaccaugaggaaau-3' |
| | | | 5 | 5'-caugugaccaugaggaaaugagaga-3' |
| | | | 6 | 5'-ccaugaggaaaugagagaaaugcuu-3' |
| | | | 7 | 5'-gagagaaaugcuuacacacagaaau-3' |
| | | | 8 | 5'-ccgcucaauuuaugaauauuaucau-3' |
| | | | 9 | 5'-cucaauuuaugaauauuaucaugcu-3' |
| | | | 10 | 5'-ggaugcuugccaaaagagguggaua-3' |

TABLE 6

Sequence templates used in the design of Her-2 targeted siRNA duplexes

| Gene homology | Length | No. | Sense Sequences |
|---|---|---|---|
| Her-2 Human (NM_004448) Mouse (M_001003817) | 21-mer | 1 | ctgcctggcctgcctccactt |
| | | 2 | ctgcgggagctgcagcttcga |

TABLE 6-continued

Sequence templates used in the design of Her-2 targeted siRNA duplexes

| Gene homology | Length | No. | Sense Sequences |
|---|---|---|---|
| | | 3 | cctggcctgcctccacttcaa |
| | | 4 | ccaggagtttgctggctgcaa |
| | | 5 | ggagtttgctggctgcaagaa |
| | | 6 | gctggctgcaagaagatcttt |
| | | 7 | caagaagatctttgggagcct |
| | | 8 | gatctttgggagcctggcatt |
| | | 9 | gatcacaggttacctatacat |
| | | 10 | ggcccacccagtgtgtcaact |
| | 23-mer | 1 | ctgcctggcctgcctccactca |
| | | 2 | gactgcctggcctgcctccactt |
| | | 3 | ccaggagtttgctggctgcaaga |
| | | 4 | gaagatctttgggagcctggcat |
| | | 5 | gagatcacaggttacctatacat |
| | | 6 | ccagggcccacccagtgtgtcaa |
| | | 7 | gcccacccagtgtgtcaactgca |
| | | 8 | gacacagcttatgccctatggct |
| | | 9 | cagattgccaaggggatgagcta |
| | | 10 | gccaaggggatgagctacctgga |
| | 25-mer | 1 | 5'-ctgactgcctggcctgcctccactt-3' |
| | | 2 | 5'-gactgcctggcctgcctccacttca-3' |
| | | 3 | 5'-caggagtttgctggctgcaagaaga-3' |
| | | 4 | 5'-gtttgctggctgcaagaagatcttt-3' |
| | | 5 | 5'-gctgcaagaagatctttgggagcct-3' |
| | | 6 | 5'-gaagatctttgggagcctggcattt-3' |
| | | 7 | 5'-ccagggcccacccagtgtgtcaact-3' |
| | | 8 | 5'-gggcccacccagtgtgtcaactgca-3' |
| | | 9 | 5'-cacagcttatgccctatggctgcct-3' |
| | | 10 | 5'-gatgggggcaaggtgcccatcaagt-3' |

The active siRNA sequences with potent silencing activity were tested in vitro:

```
hmEGFR-siRNA:    5'-GAUCAUGGUCAAGUGCUGGAUGAUA-3'
hmVEGF-siRNA:    5'-CUGUAGACACACCCACCCACAUACA-3'
hmMMP9-siRNA:    5'-CCAGUUUGGUGUCGCGGAGCACGGA-3'
hmCox-2-siRNA:   5'-GGUCUGGUGCCUGGUCUGAUGAUGU-3'
hmPDGF-siRNA:    5'-GCCUGCUGCUCCUCGGCUGCGGAUA-3'
```

The control siRNA sequence is obtained from a bacterial genomic sequence with no homology to human and mouse genomic sequences and its sense sequence is listed in the following: Cont-25-A: 5'-gaggagccuucaggauuacaagauu-3'.

The gene knockdown results can be evaluated by measuring the mRNA changes within siRNA treated cells using RT-PCR to amplify RNA isolated for the corresponding cells. Selection of the appropriate upstream and downstream primers is the initial step for evaluation of targeted gene knockdown and choice of the appropriate cell lines. RT-PCR primer sequences are designed in silico against the three selected genes, EGFR, Raf-1 and mTOR. We can select the sequences in silico. Although the homologous sequences of both human and mouse genes can be selected for RT-PCR detection, we intend to design different primer sets for detection of either human or mouse sequences differentially. The selected primer sequences designed for each species are listed as follows:

The following DNA primer designs are based on human mTOR sequence (accession number: L34075) and mouse mTOR sequence (accession number: AF152838): hmmTOR up (5'-GTTCTCCGTGAGCTGGCCATCA-3'), hmmTOR down (5'-CTTCTCTCAGACGCTCTCCCA-3').

The following DNA primer designs are based on human Raf-1 sequence (accession number: NM_001654) and mouse Raf-1 sequence (accession number: NM_009703): hmRaf-1 up (5'-CAGGACTGCTGTGTGGTCTA-3'), hmRaf-1 down: (5'-GGCGGTTGGTACTCATGTCAA-3').

The following DNA primer designs are based on human EGFR sequence (accession number: NM_005228) and Mouse EGFR sequence (accession number: AF275367): hmEGFR up (5'-CTCTGGATCCCAGAAGGTGAGA-3'), hmEGFR down (5'-GCCATCCACTTGATAGGCACTT-3').

The following DNA primer designs are based on human VEGF sequence (accession number: NM_001025366) and Mouse VEGF sequence (accession number: NM_001025250): hmVEGF up (5'-GAAGGAAGAGGAGAGGGGGCCGCA-3'), hmVEGF down (5'-GTGCAGCCTGGGACCACTTGGCAT-3').

The following DNA primer designs are based on human Her-2 sequences (accession number: NM_004448) and mouse Her-2 sequences (accession number: NM_001003817): hmHer2 up (5'-GCCTGGCCTGCCTCCACTTCAA-3'), hmHer2 down (5'-GCCAGGCTCCCAAAGATCTTCT-3').

The potent siRNA oligos targeting various genes are combined as siRNA cocktails with defined ratios. Some examples are listed below:

```
Cocktail 1:
hmEGFR-siRNA:    5'-GAUCAUGGUCAAGUGCUGGAUGAUA-3'
hmVEGF-siRNA:    5'-CUGUAGACACACCCACCCACAUACA-3'
hmMMP9-siRNA:    5'-CCAGUUUGGUGUCGCGGAGCACGGA-3'

Cocktail 2;
hmEGFR-siRNA:    5'-GAUCAUGGUCAAGUGCUGGAUGAUA-3'
hmVEGF-siRNA:    5'-CUGUAGACACACCCACCCACAUACA-3'
hmCox-2-siRNA:   5'-GGUCUGGUGCCUGGUCUGAUGAUGU-3'
```

```
Cocktail 3:
hmEGFR-siRNA:     5'-GAUCAUGGUCAAGUGCUGGAUGAUA-3' hmVEGF-siRNA:     5'-CUGUAGACACACCCACCCACAUACA-3' hmPDGF-siRNA:     5'-GCCUGCUGCUCCUCGGCUGCGGAUA-3'

Cocktail 4:       hmEGFR-siRNA + hmRaf-1-siRNA + hmmTOR-siRNA oligos

Cocktail 5:       hmEGFR-siRNA + hmRaf-1-siRNA + hmPDGF-siRNA oligos
```

There are several siRNA motifs being considered as the immune stimulatory elements when they are applied with cationic liposome or polymer carriers. These motifs include (1) 5'-UGUGU-3'; (2) 5'-GUCCUUCAA-3'. One approach is to use 25 mer siRNAs containing these motifs to modulate the immune response in addition to the siRNA-mediated gene silencing effect. These motifs can be homology sequences of the targeted mRNA sequence or added to the 19 mer siRNA duplexes.

A different approach involves taking the DNA oligos containing those immune stimulatory motifs, such as CpG motifs: 5'-GTCGTT-3', etc, or non-CpG motifs: 5'-GGGxGG__3' (where x is A, C, G or T). These DNA oligos can be added as part of the nucleic acid cocktail that has dual functions for both target gene silencing and immune stimulation. This type of the nucleic acid cocktails is packaged with liposome based or polymer based nanoparticles for treatment of breast cancer.

Endogenously expressed target genes are to be tested for the efficacy and specificity of designed siRNA duplexes in tissue culture. The first thing we intend to do is confirming the target gene expression in the working cell lines. From the preliminary studies, we know that the EGFR and Raf-1 are indeed expressed in MBA-MD-435 cells. Both genes are also expressed in MBA-MD-231 cells according to literature reports. Thus, we will verify whether the mTOR gene is truly expressed in the two cell lines. In addition, we also want to create siRNA duplexes able to knockdown the target genes in both human and mouse cells; therefore, an appropriate mouse cell line(s) will be identified and confirmed for the same reasons. Two mouse cell lines, normal mouse NIH 3T3 fibroblasts and mouse embryo endothelial cell C166, will be used for evaluation of mouse EGFR, Raf-1 and mTOR gene knockdown in vitro.

Two human cell lines, MDA-MB-435 and MDA-MB-231, and two mouse cell lines, NIH3T3 and C166, maintained in Dulbecco's Minimal Essential Medium (DMEM) containing 10% fetal calf serum (FCS) and 20 mM glutamine, will be examined for the ability of individual siRNA knockdown of a particular gene target. Cells are transfected using a Lipofectamine 2000 (Invitrogen, Calif.). Briefly, the cells are seeded (1×105 per well) in a 6-well plate in 2 ml of DMEM medium. The siRNA is diluted in 0.2 ml serum-free Opti medium, mixed with 3 μl of the transfection reagent, incubated for 30 min at room temperature, then added drop-wise into the cell culture. Target mRNA and protein levels and effects on cells are analyzed in 48 h.

Total RNA will be extracted from cell culture or tumor tissues with RNeasy mini kit (Qiagen, Valencia, Calif.) according to the manufacturer's instructions. For RT-PCR, the first cDNA strands will be synthesized by using cDNA Synthesis Kit (GE Healthcare, Chicago, Ill.) according to the manufacturer's instructions. The PCR reaction will be started with lower cycle numbers, from 25, 30 to 35 to avoid the possible amplification plateau. Both Geneamp 9700 Thermalcycler and Taqman (ABI, CA) will be used for PCR analysis. The amplicons will be subjected to gel electrophoresis analysis. To demonstrate that the levels of EGFR, Raf-1 and mTOR proteins can be down-regulated by the corresponding siRNAs, the siRNA transfected cancer cells are measured for the levels of EGFR, Raf-1 and mTOR, respectively. ELISA with specific antisera will be used for validation of siRNA-mediated down-regulation targeted proteins according to the manufacturer's instructions. Antibodies against EGFR, Raf-1 and mTOR will be purchased from CalBiochem (San Diego, Calif.), Abcam (Cambridge, Mass.), and R & D (Minneapolis, Minn.), respectively.

The cell samples will be collected after Lipo2000 mediated transfection of siRNA duplexes targeting EGFR, Raf-1 and mTOR genes for the TUNEL assay, cell autophagy assay and Ki-67 assay. Coverslips containing either harvested cells will be fixed with 4% paraformaldehyde, incubated in 0.1% Triton X-100, then with TUNEL reaction mixture (Roche Molecular Biochemicals, Penzberg, Germany) for 1 h at room temperature in darkness to allow incorporation of fluorescein (FITC)-dUTP into DNA fragments. The procedure will be completed accordingly and the slides will be analyzed with a fluorescence microscope (Nikon Eclipse E800). Cell autophagy test will be carried out with collected cells, which will be fixed with 4% paraformaldehyde and incubated in 0.1% Triton X-100. After blocked with 5% BSA for 1 hour, the cells will be incubated with a GFP antibody (Santa Cruz Biotechnology, Santa Cruz, Calif.) for 1 hour, then with an Alexa Fluor 488-conjugated secondary antibody (Invitrogen, Carlsbad, Calif.) together with Texas Red-conjugated phalloidin. The coverslips will be sealed and subjected to fluorescent microscopic analysis. Analysis of cell proliferation will be carried out with coverslips containing harvested cells incubated in 0.1% Triton X-100, and blocked with 5% BSA for 1 h, then incubated with a polyclonal antibody ab833 (Abcam, Cambridge, Mass.) against proliferating cell nuclear marker Ki-67, then with Texas Red labeled anti-rabbit antibody (Vector Laboratories, Burlingame, Calif.), then sealed, and subjected to fluorescent microscopic analysis.

HK polymers were synthesized on a Ranin Voyager synthesizer (PTI, Tucson, Ariz.) as described in Leng et al 2006, Leng et al 2007, and Leng et al, 2008 Three polymers (H3K8b, H3K(+H)4b), H3K(+G)4b) were used as siRNA carriers in this study. H3K8b has 8 terminal branches and a molecular weight of 22 922; H3K(+H)4b and H3K(+G)4b have 4 terminal branches and molecular weights of 10, 191 and 10, 539, respectively. The structures of HK polymers are as follows: R-K(R)-K(R)-K(R) where R=[HHHKHHHKH-HHKHHH]$^2$KH4NH4] for H3K8b; R=[KHHHKHHHH-KHH-HKHHH] for H3K(+H)4b; R=[KHHHKHHHKGHH-HKHHHG] for H3K(+G)4b. Nomenclature of HK polymers: 1) for H3K4b, the dominant repeating sequence in its terminal branch is -HHHK-, thus "H3K" is part of the name; the "4b" refers to the number of terminal branches; 2) for H3K(+H)4b, four-branched analog of H3K4b in which 1 extra histidine is inserted in the terminal branch of H3K4b; 3) for H3K(+G)4b, four-branched analog of H3K4b in which 2 glycines are interspersed within the dominant pattern of the terminal branch; 4) for H3K8b, an eight-branched HK polymer with a dominant terminal sequence of -HHHK-. We are going to focus on one particular species of Histidine-Lysine Polymer, H3K4b, denoted as HKP for simplification.

H3K4b (300 μg) in complex with siRNA (75 μg) (4:1 wt:wt, polymer:siRNA) will be prepared for in vivo systemic delivery into the tumor bearing mice. After the HKP carriers being prepared in $D_5W$ (5% Dextrose; 375 μl) for 30 min, water (625 μl) will be added. Particle size is determined by measurement of light scattering at a 90-degree angle on an N4 Submicron Particle Size Analyzer (Beckman Coulter, Hialeah, Fla.), and is reported as the average size obtained from a unimodal analysis carried out using the software provided by the instrument manufacturer. Each data point represents the mean+S.D. of three measurements. To make siRNA-containing nanoparticles, the siRNA (50 μg in 125 μl of $D_5W$) and HK (100, 200, 300, or 400 μg in 125 μl $D_5W$) will be added quickly and mixed briefly with a Vortex mixer. After the polyplexes are maintained for 30 min at room temperature, 250 μl of each will be injected into the tail vein of each mouse. Since there are substantial data support that the best ratio of HKP to siRNA for in vivo systemic delivery is 4:1 (wt/wt), we will maintain the optimized ratio throughout the proposed study.

Since the introduction of DOTAP, there has been a steadily increasing number of scientific articles referring to this lipid. To date, at least 400 scientific papers have been published regarding different aspects of DOTAP. There is abundant literature regarding in vitro and in vivo applications of DOTAP for nucleic acid delivery including siRNA delivery. We compare the in vivo delivery efficiencies between (S)-DOTAP Chloride and R-DOTAP-Chloride after they are packaged with active siRNA oligos with xenograft tumor models with MDA-MB-435 cell and MDA-MB-231 cells. The lipoplex-siRNA nanoparticles are analysed for the particle size, Zeta potential and other characteristics related to the stability and deliverability.

Female adult nude mice (4-6 weeks) will be obtained from NCI Frederick. MDA-MB-435 and MBA-MD-231 cells ($7\times10^5$ cells/injection) will be injected bilaterally into the mammary fat pads of each mouse. The reason to use these models instead of the estrogen dependent model like MCF-7 cell is that these models are easy to work with, usually having homogenous xenograft tumors after tumor cell inoculation. The mice are going to be separated into groups of 8-10 mice to determine efficacy of the HK in complex with EGFR, Raf-1 and mTOR siRNA duplexes. The mice will be given 4-5 intravenous injections of HKP-siRNA complex, each separated by 3-5 days (50 ∞g of siRNA/tumor/injection and various amounts of HK). Tumor size is assessed with caliper measurements of the tumors in two dimensions before each injection and 3 days after the last injection; the volume is calculated by formula $\frac{1}{2}\times length \times width^2$.

Systemic delivery of HKP-siRNA nanoparticles into the mouse xenograft tumor models achieved potent anti-tumor activity in our preliminary studies, due to an enhanced permeability and retention (EPR) effect or pH gradient effect. When this HKP aqueous solution mixed with siRNA aqueous solution at a ratio of 4:1 by mass, the nanoparticles of average size of 100-200 nm in diameter were self-assembled. The resulted HKP-siRNA solutions can be used for the tail vein injection. To evaluate the siRNA distribution using HKP-siRNA nanoparticle systemic delivery, the fluorophore-labeled (AlexaFluor 555) siRNA was used. After implanted MDA-MB-435 tumor xenografts reached 50 $mm^3$, HKP-AlexaFluor-555 siRNA will be administered by i.v. injections. Mice will be euthanized 6 hr, 24 hr, 48 hr and 72 hr later and frozen sections will be prepared from several organs (lungs, liver, spleen, kidneys and brain) and tumor xenografts. Images of these tissues will be obtained with a Diaphot-TMD fluorescence microscope fitted with a Z-motor and deconvolved with 3-D Volocity Restoration software. The half-life of HKP delivery siRNA will be examined in both tumor and other tissues. The distribution of labeled siRNA in every tissue samples will be examined for all four-time points.

Once the individual siRNA duplexes targeted to EGFR, Raf-1 and mTOR pathways are identified, we will then pursue identification of the most potent combination of the cocktail siRNAs with mouse xenograft tumor models. Several lines of experiments will be conducted. First, all individual siRNAs will be tested in the mouse models to establish a base line inhibition level. A control siRNA with non-related sequence serves as the negative control. Second, combinations of siRNAs from each target (EGFR, Raf-1 and mTOR) are generated with equal moles and tested by tail vein intravenous injection. HK polymer technique will be used in these experiments since the technique is already established in the laboratory. The synergistic activity in MBA-MD-435 and MBA-MD-231 cell xenograft tumor models will be assessed by comparing the potency of the siRNA cocktail with each individual siRNA treatment using the same dosage and dosing regimens (50 μg siRNA/200 μg HKP/per dose). The tumor growth inhibition will be measured based on the tumor size changes. Tissue samples will be collected for the measurement of the target gene silencing at the mRNA level by RT-PCR or real-time PCR. The differences between samples from the single siRNA treated group and from the control group as well as samples from the single siRNA treated group and the cocktail siRNA treated group will be compared. Either Western blot or ELISA, using antibodies against EGFR, Raf-1 and mTOR will be carried out on harvested tumor samples for further analysis of individual protein expression after siRNA treatment.

Once the most potent combination of the siRNA cocktail is determined in the xenograft model(s), we will characterize the dose curve of the treatment. The first thing to do is define the ratio of each siRNA component in the cocktail formulation. By doing so, we will identify the role of each gene targeted in the particular tumor models. Very likely, we will further define the optimal ratio for the cocktail composition and have a better understanding the relationship among these three key factors involved in breast cancer development and treatment. Second, we will characterize the dose range and therapeutic outcomes along with the dose escalation. In addition, we will further evaluate the dosing intervals with the defined ratio of each siRNA component and dosage of the siRNA cocktail in both MBA-MD-435 and MBA-MD-231 xenograft tumor models.

A 1:1:1 ratio for each of the siRNA cocktail components may not be the best choice since the expression level of individual target genes, EGFR, Raf-1 and mTOR, could be different in addition to the half life of their mRNA and proteins. Therefore, we will test the cocktails with 2:1:1, 1:2:1 and 1:2:2 ratios for the three siRNA duplexes at 50 μg dosage and three day administration interval. Under each of these conditions described in the proceeding paragraph, the dose curves are to be constructed experimentally. The upper and lower limit of the dose response will be determined by the response curves. This will determine the most effective dose that will be used in the next specific aim. After selection of the best ratio of each siRNA component, we will evaluate the dose range from 30, 60, 90, 120 μg to 150 μg per dose. At each dosing time point, a large volume of HKP-siRNA nanoparticle formulation and HKP-siRNA cocktail nanoparticle formulation will be prepared. The further dilutions will be made for each dosage with the same administration volume of 250 μl. The tumor growth curves at this time will be used as the major indicator to determine proper dosage.

With the most effective dose of siRNA cocktail against the breast cancer model determined, we will next determine the optimal dosing schedule to establish a baseline for the study described in the next section. The goal is to determine the optimal interval (in days) that can sustain the inhibitory effect of the breast cancer in mouse model. We will characterize the dosing intervals for three days, five days, and seven days for each experiment group. Each group of treatment will have the minimal number of animals to be statistically significant. The inhibitory effect will be monitored as described above. Size of the tumors will be analyzed over time. The results will be compared among the treatment groups. Criteria for the optimal dosing schedule will be calculated based on the tumor growth inhibition and knowledge of siRNA half-life.

Since the high dosages (150 ug) are going to be used during the dose finding experiment, we investigated the toxicity profile of the HKP formulated siRNA drug by monitoring several key toxicity parameters in the treated xenograft tumor models. Each individual formulated siRNA drug (EGFR, Raf-1 and mTOR) will be examined separately using their respective minimum dose. Animals are monitored for several key toxicity indicators: survival, body weight, general behavior, etc. The body weight of the animal is measured prior to siRNA drug delivery and twice a week after siRNA delivery for 35 days. A decrease in the body weight is considered as indication for toxicity. The experiment will be terminated if 20% body weight decrease is observed in 5 days after administration of siRNA drugs. The animal will be monitored daily for any abnormal behaviors such as stress and discomfort. At day 4, 10, and 35 after siRNA drug delivery, 5 mice from each groups are sacrificed for necropsy. At time of necropsy, gross observations are made, and either a partial or full set of tissues are taken for histopathological observations. At times of necropsy, clinical chemistries are also examined to determine blood cell levels and liver-specific enzymes.

It has been demonstrated that different anticancer therapies can be combined to treat breast cancer more effectively. This is particularly true for the advanced recurrent breast cancer that is metastatic. A study known as trial E2100 was conducted by the National Cancer Institute and the Eastern Cooperative Oncology Group (ECOG) to test if a combination therapy would be beneficial for the breast patients. To explore the possibility of synergistic effect that anticancer siRNA therapeutics have with existing anti-cancer treatment, we will test the effect of the combination of the siRNA cocktail targeting EGFR, Raf-1 and mTOR genes with Avastin in the same regimen. We hypothesize a possible synergistic effect because Avastin is an antagonist drug blocking VEGF function and the siRNA drug is a gene expression silencer blocking production.

Xenograft tumor bearing mice will be divided into seven groups as stated below with 8-10 mice in each group. Eighty to ninty mice will be inoculated with tumor cells to ensure 70 mice with workable tumors. Group A: procedure control, Group B: HKP-control siRNA, Group C: Avastin only, Group D: HKP-siRNA cocktail only, and Group E: Avastin combined with HKP-siRNA cocktail, Group F: Herceptin only, Group G: Herceptin combined with HKP-siRNA cocktail. Avastin and HKP-siRNA dosing should be conducted on two separate days in order to avoid administration trauma to the animal. The best dosage for HKP-siRNA cocktail will be determined from the previous preliminary study, and 5 mg/kg of Avastin is considered appropriate from a preliminary study. Additional different doses of Avastin will be tested when administered in combination with the HKP-siRNA cocktail in preliminary pilot studies. One goal of this study is to lower Avastin dosage with the combination therapy. The repeated dosing regimen will be based on the previous defined interval and frequency. The mice will be monitored for a month for the tumor volume. The average tumor volume will be calculated and plotted over time. The target gene knockdown at both mRNA and protein levels will be evaluated with RT-PCR and Western Blot. Blood samples will be collected for measurement of cytokine induction and other biomarker changes, such as ALT, AST, Bilirubin, etc. A series of histological analyses with immunohistochemical staining will be carried out.

To evaluate if the therapeutic benefit and antitumor activity are correlated to in vivo knockdown of targeted genes at protein level, the tumor samples from either MBA-MD-435 or MBA-MD-231 will be fixed with Streck for 48 hours, embedded in paraffin and the tumor sections on glass slides will be deparaffinated. Immunocytochemistry for Human EGFR, Raf-1 and mTOR will be then performed on the tumor sections. Endogenous peroxidase activity is blocked by incubating the cells with 3% $H_2O2$ in 100% methanol for 10 minutes, and the sections are then incubated with 3% goat serum for 30 minutes at room temperature. Biotin-labeled polyclonal antibody to EGFR, Raf-1 and mTOR (Santa Cruz) will be diluted 1:100 and then be added to the tumor sections at 41 C.° overnight, and horseradish peroxidase-labeled streptavidan complex (Vector, Burlingame, Calif.) will be then incubated for 30 minutes with the sections. After the chromagen diaminobenzene (DAB) is applied to the tumor sections for 10 minutes, the tumor sections are dehydrated and mounted with glass coverslips. Comparison studies will be conducted among samples from all groups.

To further explore mechanism(s) of anti-tumor activity of the combined regimen of siRNA cocktail and Avastin, tumors are fixed with 4% formalin overnight, after which tumor sections (5 μm) are deparaffinated with xylene and hydrated with ethanol. Antigens will be retrieved in 10 mM citrate, pH 6.0, by boiling for 20 min, then cooling to room temperature. Endogenous peroxidase activity is blocked by 3% $H_2O_2$ in 100% methanol for 10 min, and the sections will be then incubated with 3% goat serum for 30 min at room temperature. Antibodies against Raf-1 (Ab-259), Ki67, (1:200 dilution, Chemicon) CD31, (1:100 dilution, Cell Signal) will be added to the tumor sections for 1 h at room temperature and the secondary horseradish peroxidase-labeled antibody is applied to the sections for 30 min at room temperature (Histoscan HRP universal rabbit kit; Biomeda, cat. No. 06-602). The chromagen diaminobenzene (DAB) is incubated with the tumor sections for 10 min to permit color development, and the tumor sections are dehydrated and mounted with glass coverslips. A brown color indicates positive staining The TUNEL (terminal deoxynucleotidyl transferase) assay will be done according to the manufacturer's instructions in the FragEL DNA Fragmentation Detection Kit (Calbiochem) for the status of apoptotic activity. The TUNEL reaction mixture (deoxynucleotidyl transferase) will be incubated with the tumor section for 90 min at 37° C. in a humidified chamber. The labeling reaction will be then stopped and conjugated buffer is added to the sections for 30 min at room temperature. Then DAB substrate will be applied to the tumor sections for 10 min, the slides will be mounted with glass coverslips and examined by light microscopy.

Example 1

Use siRNA as Therapeutics to Treat Angiogenic Diseases such as Cancer and Ocular Neovascularization Diseases We have evaluated the anti-angiogenic efficacy of an siRNA cocktail targeted to VEGF pathway genes using a murine Herpetic Stromal Keratitis (HSK) model. The results of the study demonstrated our success of selection of effective siRNA sequences for the VEGF targets. In other work with local and systemic administrations of nanoparticle-siRNA in inhibition of anti-angiogenic activity, our research data also showed that the siRNA cocktail targeted to three genes is much more potent than a single siRNA species targeted to only one gene. In other work, we further demonstrated that Histidine-Lysine Polymers (HKP) can greatly enhance the therapeutic efficacy of the siRNA in the animal disease models. Thus, we select vehicles, including but not limited to HKP, to deliver the formulated multi-targeted siRNA cocktail targeted to EGFR, Raf-1 and mTOR simultaneously. Our preliminary results demonstrated that delivery of siRNA targeting Raf-1 using HK polymer worked pretty well with a breast tumor xenograft model; a similar effect was also observed with EGFR targeted siRNA using the same xenograft tumor model.

Further, we found out that 25 mer siRNA duplexes appeared to be more potent than 21 mer siRNA duplexes for their inhibitory activities in several cell culture experiments; therefore, 25 mer siRNA duplexes will be designed, tested and used in the in vivo studies. We also tested our siRNA therapeutics and Avastin (Genentech, Calif.) in a combined regimen using a xenograft tumor model, achieving a marked synergistic therapeutic efficacy. Thus, we believe there is a great potential success to combine our siRNA cocktail and Avastin in cancer treatment.

Example 2

Selection of Potent SiRNA Duplexes and Nanoparticle Formulations

The following figures demonstrated the identification of potent siRNA duplexes targeting each of the genes.

In FIG. 1, RT-PCR analyses for mRNA levels of mVEGF, mVEGFR1 and mVEGFR2 after treatment of nanoparticle containing potent SiRNA duplexes. All nanoparticle-containing potent SiRNA duplexes demonstrated their potent activities to knockdown their targeted genes, compared to the control siRNA duplexes, siC1ab in FIG. 1(*a*). Formations of two different types of polymeric siRNA nanoparticles are shown in FIG. 1(*b*). In short, HKP-siRNA particles can be formed when HKP aqueous solution is mixed with siRNA solution, and so does the RPP-siRNA particles. Local and systemic administrations of siRNA nanoparticles are illustrated in FIG. 1(*c*). In short, HKP-siRNA particles were mainly for local deliveries through either subconjunctival (SCJ) or intravitreous (IVT) route. RPP-siRNA particles were applied for systemic deliveries through either intraperitoneal (IPT) or intravenous (IVN) routes, respectively, reaching to the blood stream first and then the ocular neovasculature.

Example 3

Cocktail siRNA Exhibited Stronger Anti-Angiogenesis Activity

Figure 2:
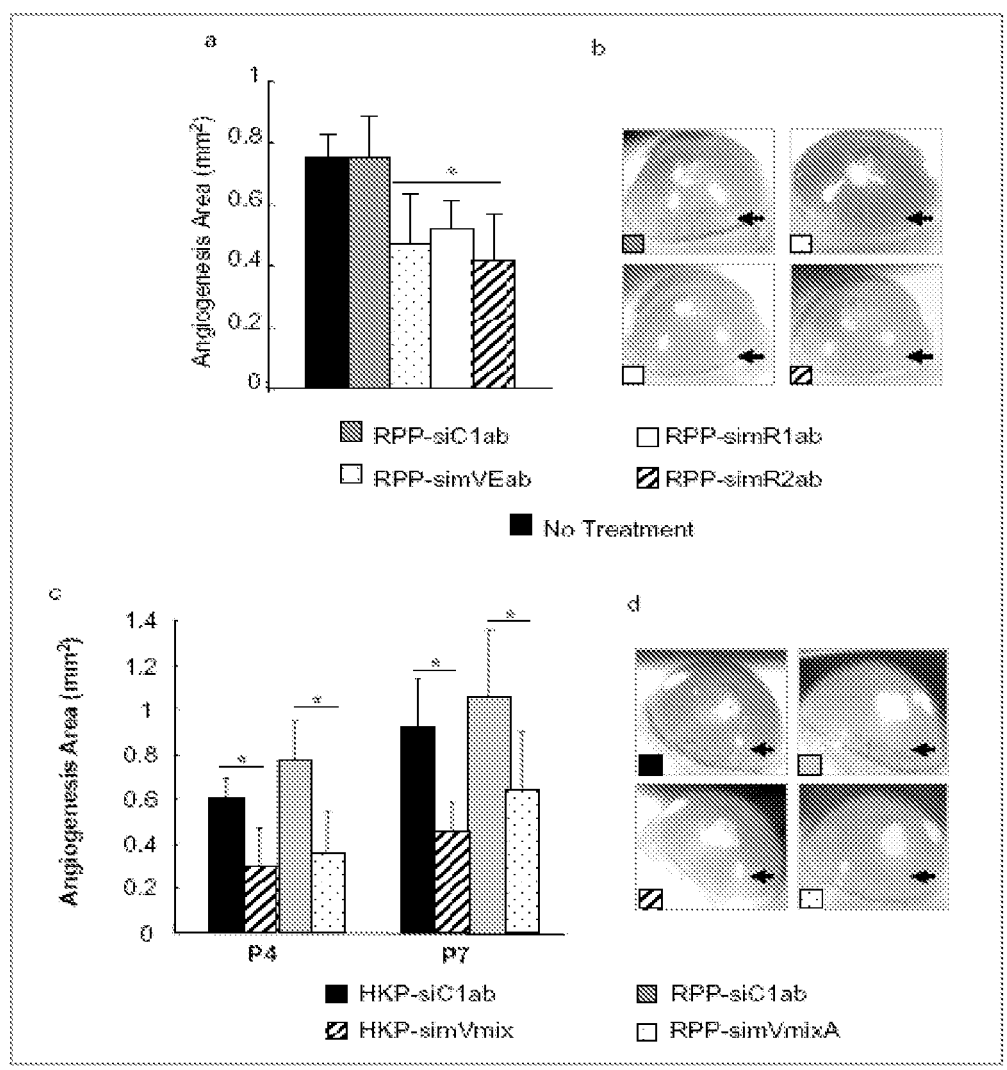
FIG. 2. Cocktail siRNA exhibited strong anti-angiogenesis efficacy on CpG induced ocular NV. (a) Systemic delivery (IVN) of RPP-carried simVEab (dot), simR1ab (blank) and simR2ab (stripe) significantly minimized angiogenesis areas in mouse eyes at P4 (*P<0.05, n=8) compared to RPP-siC1ab treated group (grey) and no treatment group (black). (b) Images from mouse eyes representing each treated group marked with the same pattern as (a). (c) At both P4 and P7, both locally (SCJ) delivered HSK-simVmix and systemically (IVN) delivered RPP-simVmix demonstrated potent anti-angiogenesis efficacy. The angiogenesis areas of the treated groups (dot and stripe) are significantly smaller compared to the HKP-siC1ab and RPP-siC1 treated groups (black and grey), with N=8, and * represents P<0.05. (d) Images of the mouse eyes from both treated and control groups, indicated by the same marks as (c).

In the experiment shown in FIG. 2, systemically delivered RPP-simVEab, -simR1ab and -simR2ab nanoparticles (40 μg/100 μl/eye) containing specific siRNA duplexes significantly minimized angiogenesis areas in mouse eyes compared to the no treatment and siC lab treated groups. In another experiment, treatment of cocktail siRNA nanoparticles, HKP-simVmix (4 μg/2 μl/eye) through SJV injection and RPP-simVmix (40 μg/100 μl/eye) through IVN injection resulted in stronger anti-angiogenesis activities in the HSK models, at both P4 and P7, through either local or systemic delivery.

Example 4

Systemic Delivery of HKP Nanoparticle-Encapsulated siRNA to Xenograft Tumors

In this experiment (FIG. 3A), we demonstrated that the fluorescein-labelled siRNA molecules reached the interior of tumors within the first minute after injection, when the main body of the siRNA was found in the lung. By 60 minutes, a readily detectable amount of siRNA molecules were found in the tumors as well as in the kidney. In another experiment, we showed that the siRNA molecules were mostly deposited in proximity to the tumor vasculature (FIG. 3B), indicating that intravenous delivery of the HKP nanoparticle-encapsulated siRNA can gave rise to significant enrichment of the siRNA in tumor tissues.

Example 5

HKP Nanoparticle-Encapsulated EGFR siRNA Inhibits Xenograft Tumor Growth

Figure 4:
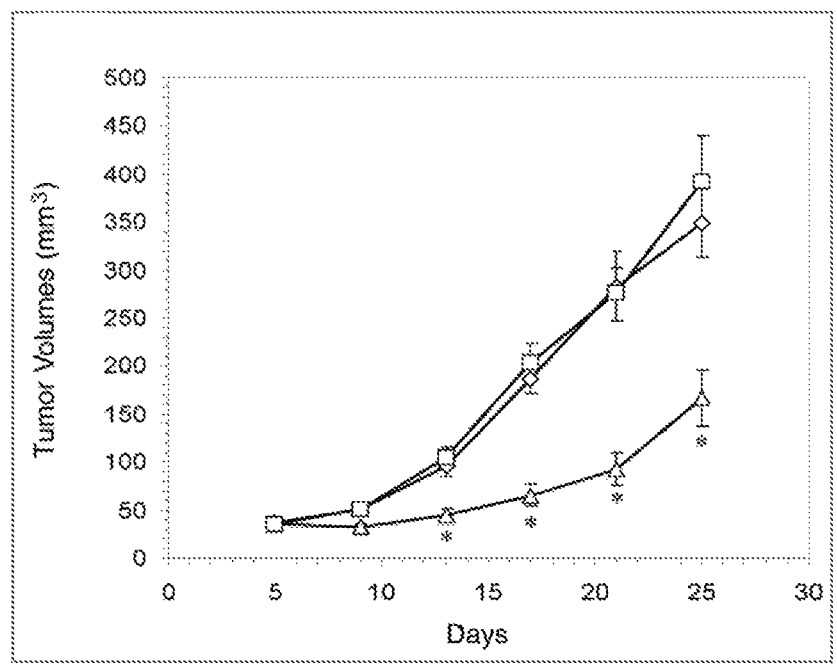
FIG. 4. Inhibition of MBA-MD-435 cell induced xenograft tumor growth by intravenously injected EGFR siRNA. Plots of MBA-MD-435 tumor volumes as a function of time. The tumor-bearing mice were given various HKP-EGFR siRNA mixtures via tail vein injection with 5 days intervals as indicated: Diamonds, vehicle treated (n=6); Squares, control siRNA CT-1 (n=6); Triangles, EGFR siRNA (n=6). The treatment was initiated on Day 10 when the tumors became palpable and repeated once every 5 days for a total of 5 times. Asterisks, p<0.01, ANOVA. The experiment was repeated once under identical conditions and the results were reproducible.

In this experiment (FIG. 4), we demonstrated that inhibition of MBA-MD-435 cell induced xenograft tumor growth by intravenously injected EGFR siRNA by ANOVA ($p<0.01$).

Example 6

Systemically Delivered HKP-Raf-1 siRNA Marked Tumor Growth Reduction

Figure 5:
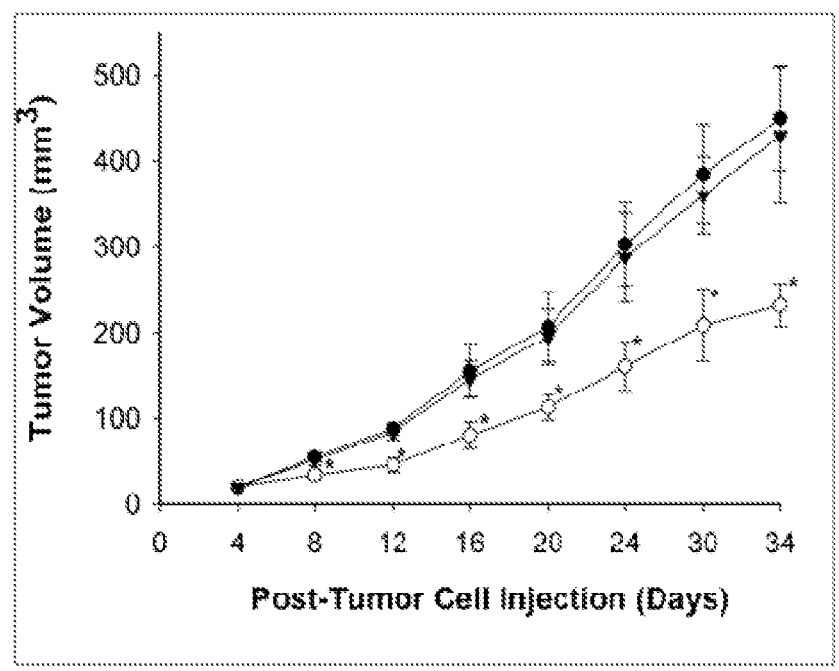
FIG. 5. Systemic injection of HKP:Raf-1 siRNA polyplex into athymic nude mice bearing MBA-MD-435 tumors. Tumor volume ($mm^3$) was measured in the groups (untreated-close circles, control siRNA-close inverted triangles, or Raf-1 siRNA open circles) before to each treatment injection time. After the tumors became visible, HKP (200 g) in complex with siRNA (50 g) were injected every 4 days for seven injections. By the second injection, there was a significant difference between the control siRNA and Raf-1 siRNA groups. *, P<0.01. One-way analysis of variance with multiple comparisons versus control siRNA or untreated group (Bonferroni's t-test).

In this experiment, there was a 40% reduction in tumor size between the HK/Raf-1 polyplex and the untreated control group (FIG. 5, $p<0.01$) after the first injection of HKP in complex with Raf-1 siRNA (50 μg). In another experiment, there was nearly a 50% difference between the control and Raf-1 siRNA treatment groups (FIG. 5, $P<0.01$, untreated, control siRNA vs. Raf-1 siRNA) after the third injection.

Example 7

Figure 6:
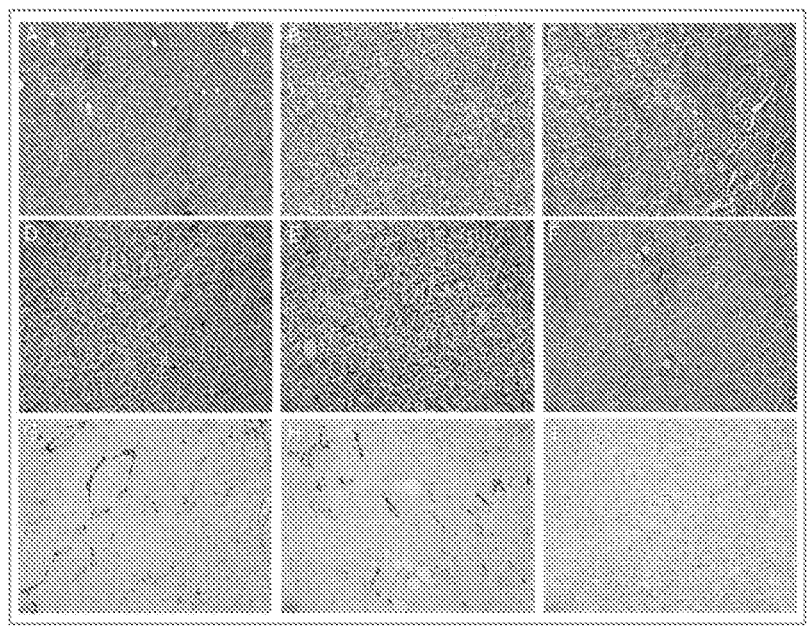
FIG. 6. Histologic and immunohistochemical analysis of CD31 and Raf-1 content of tumor xenografts. Hematoxylin and eosin staining of tumors excised from mice after various treatments (A, untreated; B, control siRNA; C, Raf-1 siRNA). Immunohistochemical staining detection of Raf-1 expression (D, untreated; E, control siRNA; F, Raf-1 siRNA). A diaminobenzidine substrate was used to visualize antibody binding to Raf-1 and is shown as the dark brown precipitate. Immunohistochemical staining detection of CD31 to determine vessel content within treatment groups (G, untreated; H, control siRNA; I, Raf-1 siRNA).
Figure 7:
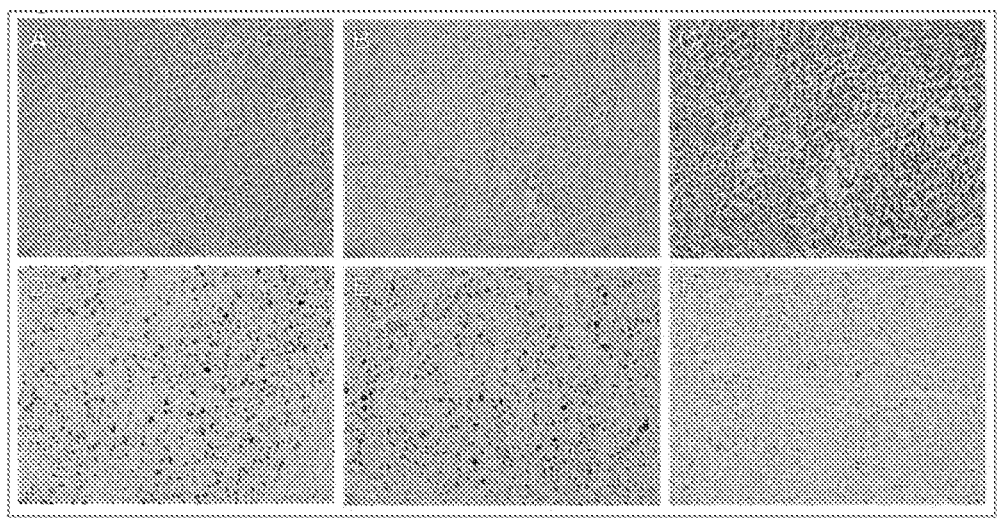
FIG. 7. Assays of cell proliferation and apoptosis of tumors after Raf-1 siRNA treatment. Apoptosis of tumor induced by Raf-1 siRNA (C), control siRNA (B), or untreated (A) as determined by TUNEL assay. Detection of Ki67 as an indicator of proliferation of tumor cells within various treatment groups (D, untreated; E, control siRNA, F, Raf-1 siRNA) ×100 magnification. Proliferation and apoptotic indices were calculated by counting positive cells in four random fields at ×100 magnification from untreated (black), control siRNA-treated (red), and Raf-1 siRNA-treated (green) mice (G) (P<0.001, untreated, Control siRNA vs. Raf-1 siRNA, One-way analysis of variance with multiple comparisons versus control siRNA and untreated groups (Bonferroni's t-test).

HKP:Raf-1 siRNA Nanoparticle Induces Marked Histological and Immununochemical Changes In this experiment, histology and immunological staining studies showed marked antitumor effects in the HKP containing Raf-1 siRNA treatment group (FIG. 6). In another experiment, decreased proliferation and increased apoptosis were observed in the Raf-1 siRNA-treated group (FIG. 7). Our data showed that the proliferation marker, Ki67, was decreased by nearly 50% within tumor sections whereas apoptosis increased by nearly 700% ($P<0.001$, untreated, control vs. Raf-1 siRNA).

Example 8

Twenty-Five mer siRNA is More Potent than Twenty-One mer siRNA

Figure 8:
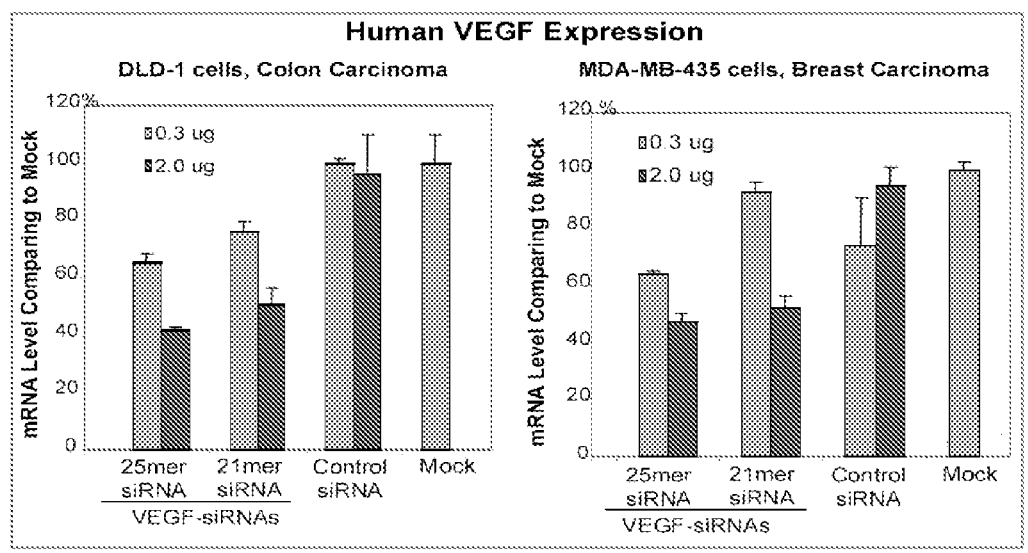
FIG. 8. Comparison of silencing potencies between 25 mer and 21 mer siRNA duplexes. The most potent 25 mer and 21 mer siRNA were selected first from each set of 6 duplexes. Than comparison was carried out with two tumor cell lines expressing human VEGF protein (DLD-1, colon carcinoma and MBA-MD-435, breast carcinoma) using in vitro transfection with Lipo2000 (Invitrogen, Calif.) followed by RT-PCR analyses. At either 0.3 μg or 2.0 μg doses, 25 mer siRNA demonstrated stronger inhibitory activity than 21 mer siRNA, especially at 2.0 μg.

In this experiment (FIG. 8), our data showed that the 25 mer blunt end siRNA is more potent than the 21 mer sticky end siRNA.

Example 9

Functional Test of Raf-1 siRNA

Figure 9:
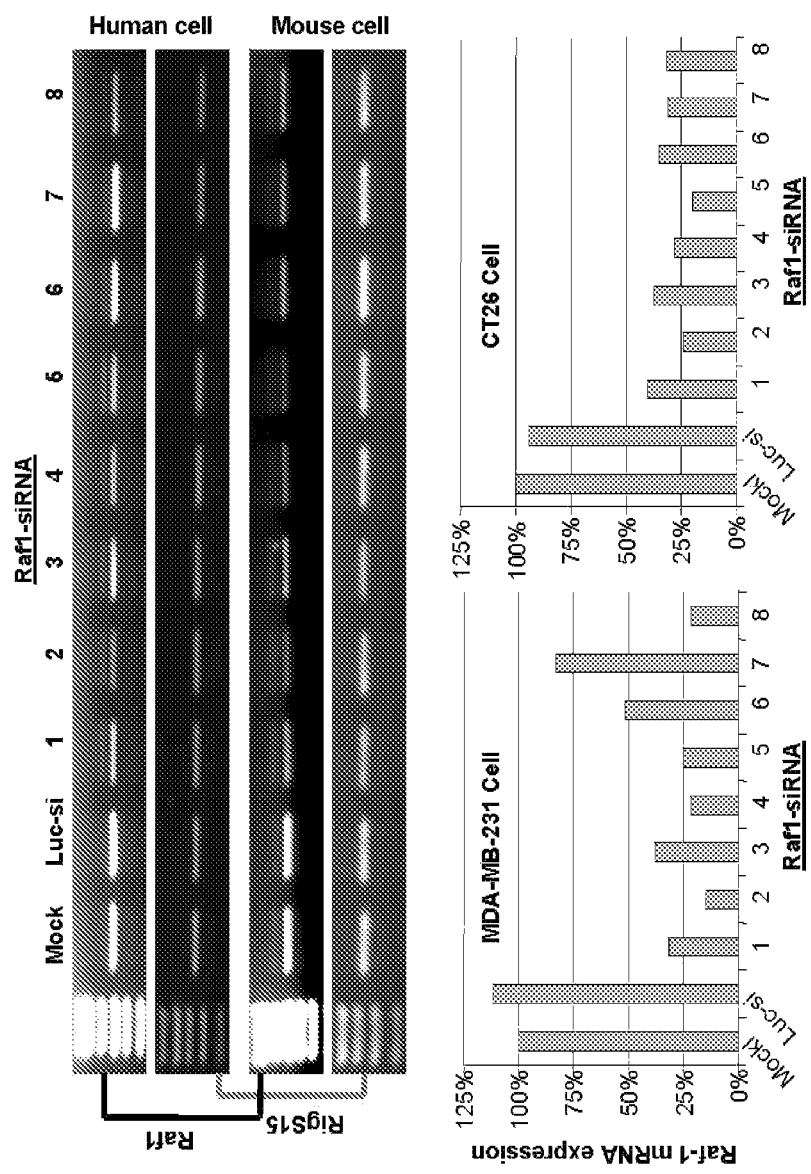
FIG. 9. Selection of potent siRNA targeting RAF-1. Gel electrophoresis for selection of potent silencer when eight 25 mer siRNA duplexes with control siRNA were transfected into human MDA-MB-231 cells and mouse CT26 cells. 24 hr later, mRNA were collected and subject to Q-RT-PCR with the standard control gene target Rigs15. Quantitative analysis based on the PCR data. Based on the gene silencing activity observed, the most potent Raf1-siRNA was selected as a component of future siRNA cocktail for both in vitro and in vivo study. For example: RAF-1-siRNA: 5'-CCUGUGGC-UACAAGUUCCACCAGCA-3' is the selected potent siRNA inhibitor.

In FIG. 9, we demonstrated designed Raf-1 siRNA was able to silence Raf-1 mRNA expression in both human MDA-MB-231 cells and mouse CT26 cells.

Example 10

Functional Test of mTOR siRNA

Figure 10:
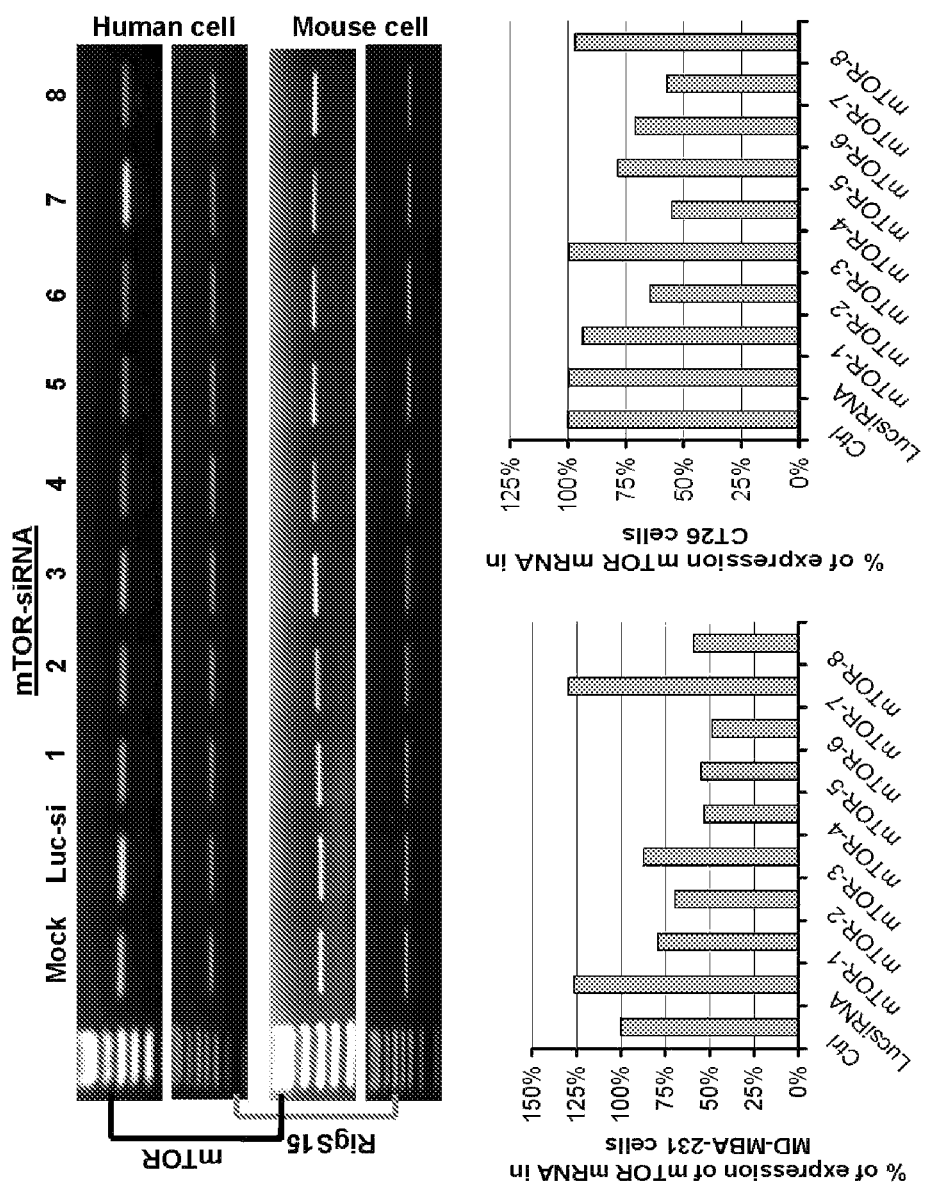
FIG. 10. Selection of potent siRNA targeting mTOR. Gel electrophoresis for selection of potent silencer when eight 25 mer siRNA duplexes with control siRNA were transfected into human MDA-MB-231 cells and mouse CT26 cells. 24 hr later, mRNA were collected and subject to Q-RT-PCR with the standard control gene target Rigs1. Based on the gene silencing activity observed, the most potent mTOR-siRNA was selected as a component of future siRNA cocktail for both in vitro and in vivo study. For example, mTOR-siRNA: 5'-CACUACAAAGAACUGGAGUUCCAGA-3' is selected as a potent silencer.

In FIG. 10, we demonstrated designed mTOR siRNA was able to silence mTOR mRNA expression in both human MDA-MB-231 cells and mouse CT26 cells.

Example 11

Functional Test of EGFR siRNA

Figure 11:
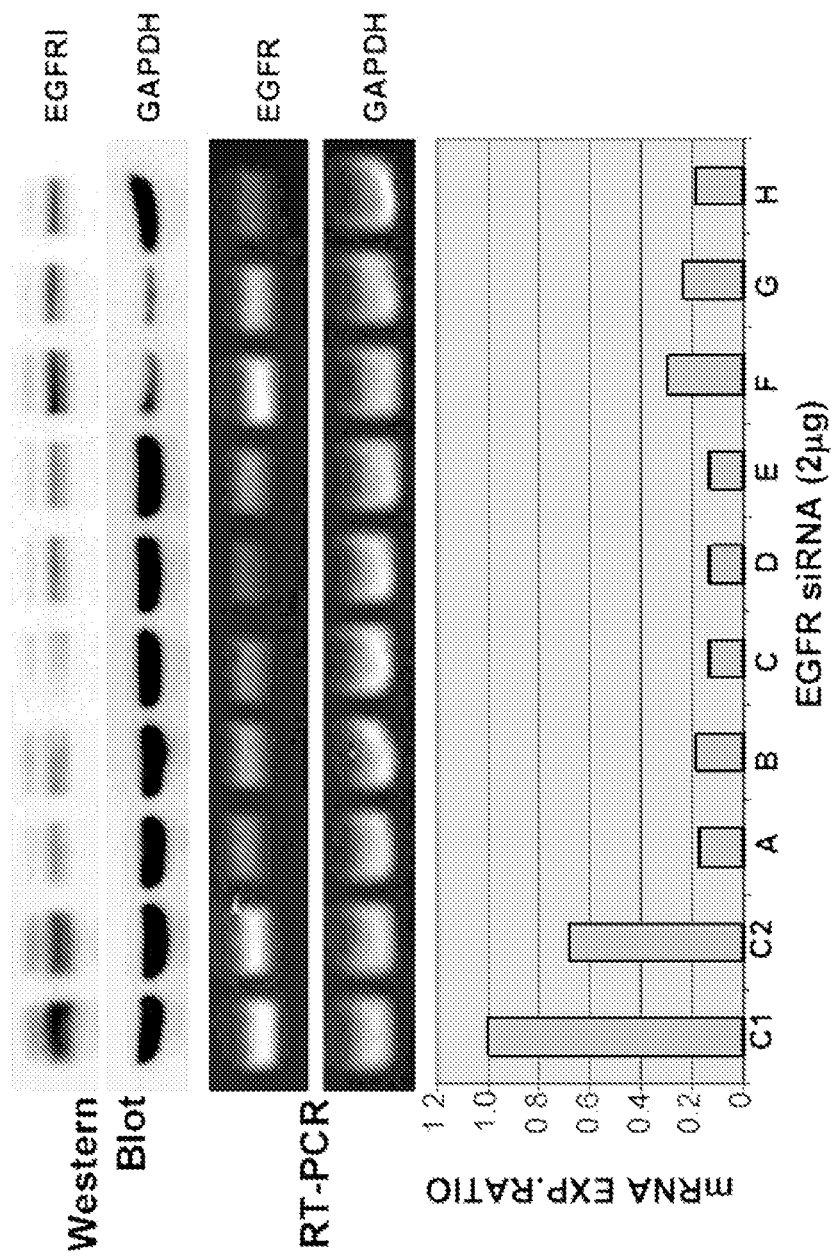
FIG. 11. Selection of potent siRNA targeting EGFR. (A) Eight 25 mer siRNA duplexes were transfected into human H898 tumor cell lines. 24 hr later, mRNA and protein samples were collected for Q-RT-PCR and Western blot analysis. (B) Quantitative analysis for potent siRNA selection for silencing EGFR. Based on the gene silencing activity observed, EGFR-siRNA-C was selected as a component of future siRNA cocktail for both in vitro and in vivo study. For example, EGFR-siRNA: 5'-GAUCAUGGUCAAGUGCUGGAUGAUA-3' is selected as the most potent silencer.

In FIG. 11, we demonstrated designed EGFR siRNA was able to silence EGFR mRNA expression in human H898 tumor cell lines.

Example 12

Functional Test of VEGF siRNA

Figure 12:
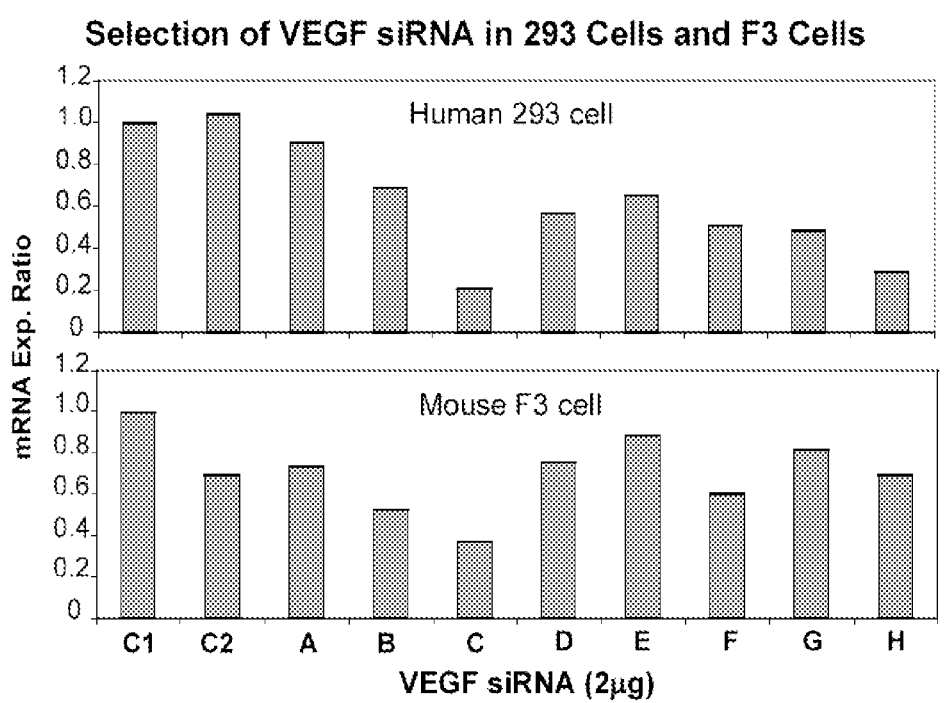
FIG. 12. Selection of potent siRNA against VEGF. Eight 25 mer siRNA duplexes were transfected into human 293 cell and mouse F3 cells. The profiles of siRNA silencing activities are very similar that VEGF-siRNA-C is also the most potent for both human and mouse VEGF gene silencing. Therefore, the most potent siRNA was selected for future siRNA cocktail. For example, VEGF-siRNA: 5'-CUGUAGACACAC-CCACCCACAUACA-3" was selected as the most potent silencer for VEGF.

In FIG. 12, we demonstrated designed VEGF siRNA was able to silence VEGF mRNA expression in both human 293 cell and mouse F3 cells.

Example 13

Functional Test of PDGF and Cox-2 siRNA

Figure 13:
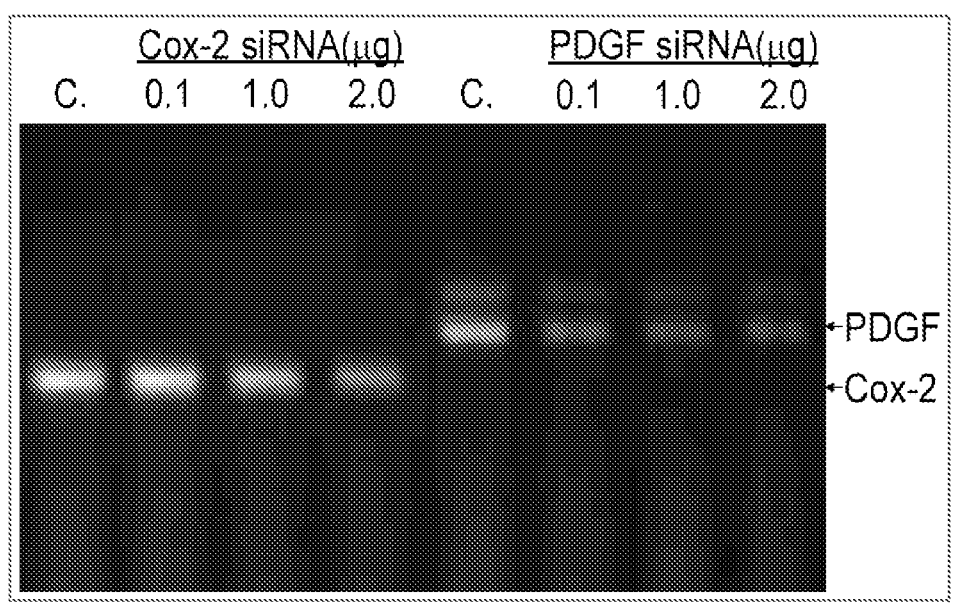
FIG. 13. Selection of the most potent siRNA targeting PDGF. The most potent siRNA duplexes target either Cox-2 or PDGF were selected. A dose dependent experiment was carried out at 0.1, 1 and 2 mg level with corresponding cell transfection followed by Q-RT-PCR analysis. C represents the control siRNA duplex. For example PDGF-siRNA-B: 5'-GCCUGCUGCUCCUCGGCUGCGGAUA-3' and Cox-2-siRNA-A:5'-GGUCUGGUGCCUGGUCUGAUGAUGU-3' were selected for the most potent siRNA silencer.

In FIG. 13, we demonstrated dose dependent effect of PDGF and Cox-2 siRNA.

Example 14

Self-Assembling of Histidine-Lysine Polymer (HKP) for siRNA Delivery

Figure 14:
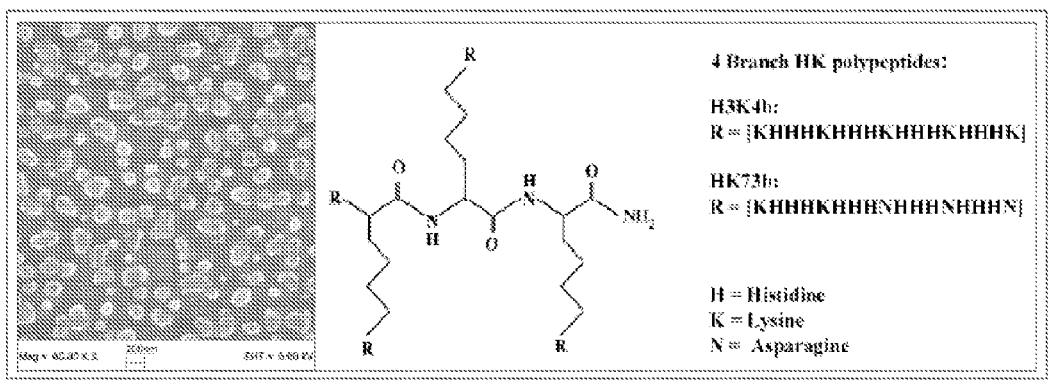
FIG. 14. Histidine-Lysine Polymer for in vivo siRNA Delivery. When HKP is mixed with siRNA in the aqueous solution, HKP-siRNA nanoparticle was self-assembled as seen in the left panel. It is observed with Scanning Electron Microscope (SEM). Two species of HKP may be applied in the local and systemic siRNA delivery for treatment of breast cancer.

In FIG. 14, we demonstrated HKP-siRNA nanoparticles were self-assembled with Scanning Electron Microscope (SEM) shown.

Example 15

Tumor Cell Viability Study with siRNA Combinations

Figure 15:
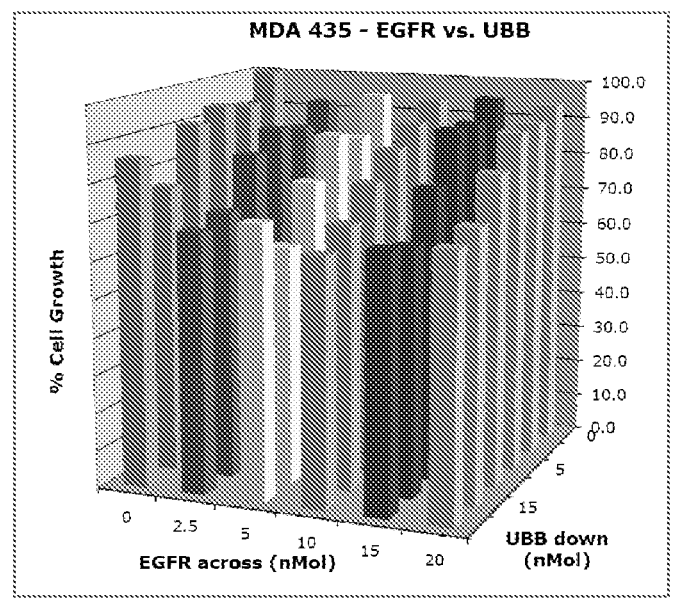
FIG. 15. Tumor Cell Viability Study with siRNA Combinations. Using MDA-MB-435 cells in culture, together with optimized transfection conditions with a lipid based Dharmafect1 (ThermoFisher, Dharmacon, Lafayette, Colo.), we examined the viability of MDA-MB-435 cells after exposure to two siRNA duplexes, EGFR-siRNA+UBB-siRNA showing additive responses of gene silencing.

In FIG. 15, we demonstrated MDA-MB-435 cells treated by two siRNA duplexes, EGFR-siRNA+UBB-siRNA, showing additive responses of gene silencing.

Example 16

Synergistic Therapeutic Benefit of the Cocktail siRNA

Figure 16:
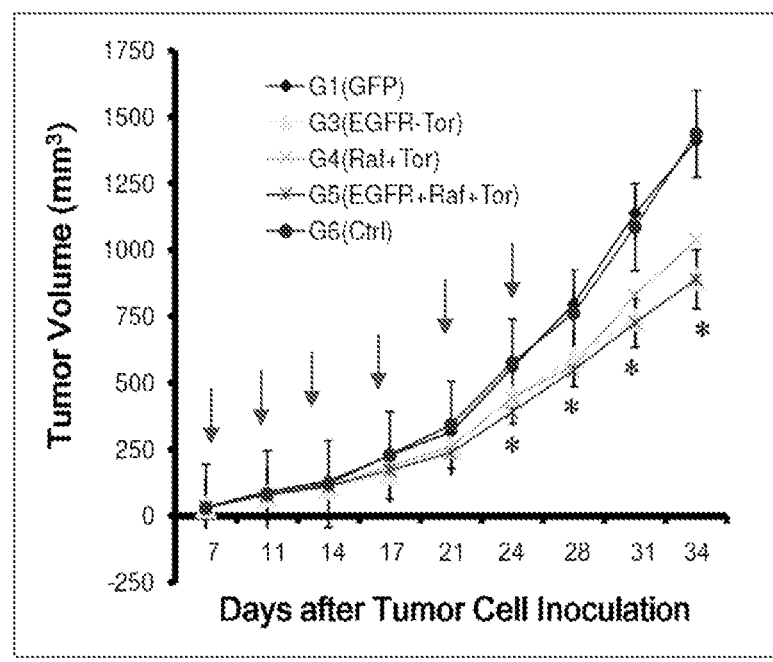
FIG. 16. Synergistic therapeutic benefit of the cocktail siRNA. Combining systemic delivery of cocktail siRNA treatment using HKP-mediated delivery in MDA-MB-435 xenograft tumors. Targeting three tumorigenic genes resulted more potent tumor growth inhibition in vivo. For example, EGFR-siRNA+mTOR-siRNA+RAF-1-siRNA combination is more potent than other treatment using single or double siRNA duplexes.

In this experiment, we demonstrated that EGFR-siRNA+mTOR-siRNA+RAF-1-siRNA combination is more potent than other treatment using single or double siRNA duplexes shown in FIG. 16.

Example 17

Synergistic Therapeutic Benefit of the Cocktail siRNA

Figure 17:
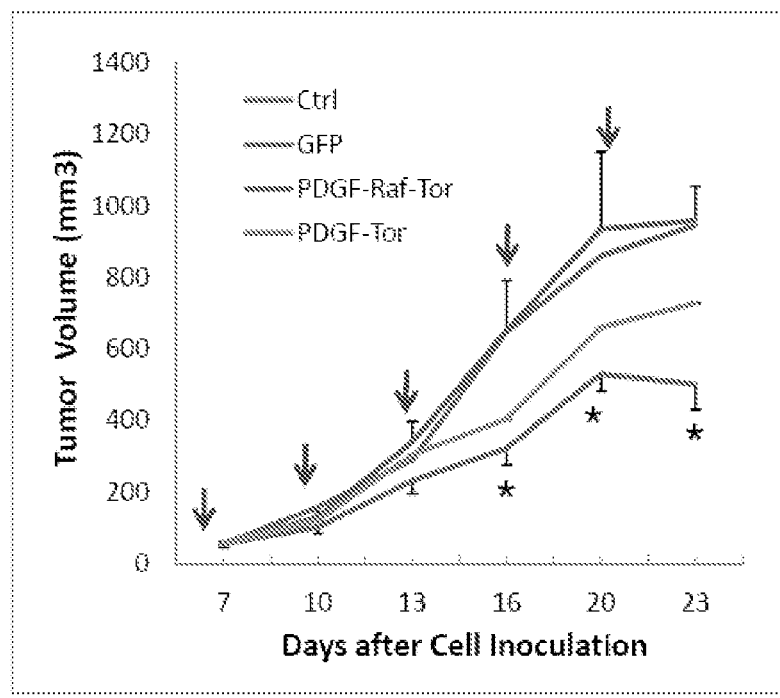
FIG. 17. Synergistic therapeutic benefit of the cocktail siRNA. Combining systemic delivery of cocktail siRNA treatment using HKP-mediated delivery in MDA-MB-435 xenograft tumors. Targeting three tumorigenic genes resulted more potent tumor growth inhibition in vivo. For example, PDGF-siRNA+mTOR-siRNA+RAF-1-siRNA combination is more potent than other treatment using single or double siRNA duplexes.

In another experiment, we demonstrated that PDGF-siRNA+mTOR-siRNA+RAF-1-siRNA combination is more potent than other treatment using single or double siRNA duplexes in MDA-MB-435 xenograft tumors shown in FIG. 17.

SiRNA Cocktail Therapeutics for Breast Cancer

Human disease is a complicated pathological process showing various severities of disease symptoms. Many human diseases are caused by abnormal over-expression of disease-causing or disease-control genes from human body itself, or from foreign infectious organisms, or both. The disease progression and development of drug resistance can also circumvent the effect of single drug treatment. Our strategy to overcome those hurdles is using combinations of multiple drugs.

The invention provides a therapeutic siRNA cocktail targeting multiple disease controlling genes in the same treatment. The invention provides for RNAi agents, such as siRNA oligonucleotides, that are chemically similar from the same source of supply and the same manufacturing process, and they are comprised of four types of nucleotides with different sequences. The invention provides the siRNA cocktail drug for treatment of breast cancer, acting on multiple aspects of the diseases and reducing potential toxicity.

This invention includes the following characteristics of the siRNA cocktail and its applications in the experimental and therapeutic settings:

The siRNA cocktail preferably contains at least three siRNA duplexes targeting at least three genes (not three sequences of the same gene) at a therapeutically effective ratio. The siRNA cocktail design for each combination follows the understanding of the role of each gene in the system biology network, such as whether the genes are functioning either in the same pathway or in different ones.

The chemical property of each siRNA duplex in the cocktail is the same in terms of source of supply, manufacturing process, chemical modification, storage conditions and formulation procedures.

Each individual siRNA duplex in the cocktail is preferably 25 mer. Since the siRNA cocktail is targeted to multiple genes and a single cell type usually does not express all those genes, the efficacy of the siRNA cocktail is tested in a relevant disease model, either a multiple cell model, a tissue model or an animal model, after the confirmation of the potency of each individual siRNA duplex in cell culture.

The siRNA cocktail is administrated through the same route of delivery in the same formulation, although the regimen of dosing for each cocktail will be defined based on either the experimental design or therapeutic requirement. Each siRNA cocktail can be applied either independently, or in combination with other drug modalities, such as small molecule inhibitors, monoclonal antibodies, protein and peptides, and other siRNA cocktail drug(s).

Experimental Design:

The design is summarized for the experiments that may be performed to evaluate the anti-tumorigenic effects of this method.

Experiment A.

To select the most potent siRNA duplexes targeted to EGFR, Raf-1 and mTOR genes, siRNA duplexes targeted to the conserved regions shared by both mouse and human will be created by in silico design followed by functional assays in vitro and in vivo to validate their efficacy. This approach will ensure both human and mouse corresponding genes can be silenced when an siRNA duplex is used in a mouse xenograft tumor model. Another advantage of the design is that the selected siRNA drug is able to avoid the issues of species specificity and cross-reaction of cytokine effects. Two human cell lines, MDA-MB-435 and MDA-MB-231, and two mouse cell lines, NIH3T3 and C166, are selected for in vitro siRNA assays. RT-PCR and ELISA assays will be used to define mRNA and proteins expression levels in the siRNA assays. Analyses of cellular apoptosis, autophagy and proliferation will also be conducted to further characterize the effects of siRNA treatment.

Experiment B.

To identify the most potent siRNA cocktail using MBA-MB-435 and MBA-Md-231 xenograft tumor models, three polymers (H3K8b, H3K(+H)4b), H3K(+G)4b) will be used as siRNA carriers in the studies. Our previous data indicate that the best ratio of HKP to siRNA for in vivo systemic delivery is 4:1 (wt/wt); thus, we will keep using the same ratio throughout the studies. Female adult nude mice (4-6 weeks) were obtained from NCI Frederick. MDA-MB-435 and MBA-MD-231 cells ($7 \times 10^5$ cells/injection) were injected bilaterally into the mammary fat pads of each mouse. The mice are going to be separated into groups of 8-10 mice to determine efficacy of the HK in complex with EGFR, Raf-1 and mTOR siRNA duplexes. The mice will be given 4-5 intravenous injections of HKP-siRNA complex, each separated by 3-5 days (50 μg of siRNA/tumor/injection and various amounts of HK). HKP aqueous solution will be mixed with siRNA aqueous solution at a ratio of 4:1 by mass, the nanoparticles will be self-assembled at the average size of 100-200 nm in diameter. The resulting HKP-siRNA solutions can be used for the tail vein injections. To evaluate the siRNA distribution by HKP-siRNA nanoparticle systemic delivery, fluorescein-labelled (AlexaFluor 555) siRNA will be administered by i.v. injections after implanted MDA-MB-435 tumor xenografts reach 50 mm$^3$. Mice will be euthanized 6 h, 24 h, 48 hr and 72 h later and frozen sections will be prepared from several organs (lungs, liver, spleen, kidneys and brain) and tumor xenografts. Images of these tissues will be obtained with a Diaphot-TMD fluorescence microscope fitted with a Z-motor and deconvolved with 3-D Volocity Restoration software. Once the individual siRNA duplexes targeted to EGFR, Raf-1 and mTOR pathways are validated, we will identify the optimal combination of the cocktail siRNAs by mouse xenograft tumor models. Western blot or ELISA will be use to further characterize EGFR, Raf-1 and mTOR protein expression in the multi-targeted siRNA cocktail treated tumor tissues.

Experiment C.

Characterization of siRNA cocktail targeted to EGFR, Raf-1 and mTOR genes. After the most potent combination of the siRNA cocktail is determined by the xenograft model(s), we will characterize the dose curve of the treatment. We will test the cocktails with 2:1:1, 1:2:1 and 1:2:2 ratios for the three siRNA duplexes at 50 μg dosage and three day administration interval. After selection of the best ratio of each siRNA component, we will evaluate the dose range from 30, 60, 90, 120 μg to 150 μg per dose. At each dosing time point, a large volume of HKP-siRNA nanoparticle formulation and HKP-siRNA cocktail nanoparticle formulation will be prepared. The next goal is to determine the optimal interval (in days) that can sustain the inhibitory effect of the breast cancer in the mouse model by characterizing the dosing intervals for three days, five days, and seven days for each experiment group followed by statistical analysis. Finally, each individually formulated siRNA drug (EGFR, Raf-1 and mTOR) will be examined separately for several key toxicity indicators: survival, body weight, general behavior, etc.

Experiment D.

Combine siRNA cocktail therapeutics with monoclonal antibody Avastin for treatment of breast cancer in two animal models. We will test the effect of the combination of the siRNA cocktail targeted to EGFR, Raf-1 and mTOR genes with Avastin in the same regimen. Avastin is an antagonist drug blocking VEGF function, whereas the siRNA drug is a gene expression silencer blocking the production of three proteins, including VEGF, simultaneously. We will determine if there is a synergistic effect for treatment of cancer in the combination of both. In one experimental design, xenograft tumor-bearing mice will be divided into seven groups with 8-10 mice in each group. Eighty to ninty mice will be inoculated with tumor cells to ensure 70 mice with workable tumors. Group A: procedure control, Group B: HKP-control siRNA, Group C: Avastin only, Group D: HKP-siRNA cocktail only, Group E: Avastin combined with HKP-siRNA cocktail, Group F: Herceptin only, and Group G: Herceptin combined with HKP-siRNA cocktail. (Herceptin is included in the study as a comparison reference.) The target gene knockdown at both mRNA and protein levels will be evaluated with RT-PCR and Western Blot. In another experiment designed for evaluation of therapeutic benefit and antitumor activity in vivo, the tumor samples from either MBA-MD-435 or MBA-MD-231 will be analyzed by immunohistochemical staining Histology analyses and the tunnel assay will also be conducted to further investigate mechanisms of anti-tumor activity of the siRNA cocktail and Avastin combination regimen.

REFERENCES

1. Deshpande, S. P. et al, (2002), Vet. Microbiol, 86: 17-26.
2. Leng, Q., et al. A branched histidine/lysine peptide, H2K4b, in complex with plasmids encoding antitumor proteins inhibits tumor xenografts. J Gene Med, 8: 1407-1415, 2006.
3. Hood J. et al. Protein kinase G mediates vascular endothelial growth factor-induced Raf-1 activation and proliferation in human endothelial cells. J Biol Chem 1998; 273: 23504-23508.
4. Schiffelers R. M. et al. Cancer siRNA therapy by tumor selective delivery with ligand-targeted sterically stabilized nanoparticle. Nucleic Acids Res 2004; 32:e149.
5. Li B. J., et al. Using siRNA in prophylactic and therapeutic regimens against SARS coronavirus in Rhesus macaque. Nat Med 2005; 11:944-951.
6. Song E., et al. Antibody mediated in vivo delivery of small interfering RNAs via cell-surface receptors. Nat Biotechnol 2005; 23:709-717.
7. Leng Q., et al. Histidine-lysine peptides as carriers of nucleic acids. Drug News Perspect 2007; 20:77-86.
8. Benjamin L E, et al (1997), PNAS, 94: 86571-8766.
9. Cao Y, et al, (1998), PNAS, 95: 14389-14394.
10. Elbashir A M, et al, Duplexes of 21-nucleotide RNAs Mediate RNA Interference in Cultured Mammalian Cells, Nature, 411: 494-8 (2001a).
11. Elbashir S M, et al, Functional Anatomy of siRN as for Mediating Efficient RNAi in *Drosophila Melanogaster* Embryo lysate, EMBO, 20 (23): 6877-6888 (2001b).
12. Eriksson U & Alitalo, K, Structure, Expression and Receptor-binding Properties of Novel Vascular Endothelial Growth Factors, Curr. Top. Microbiol. Immunol. 237: 41-57 (1999).
13. Ferrara, N, (1999), Annu Rev. Med. 49:407.

14. Eriksson, A., et al, (2002), Cancer Cell, 1: 99-108.
15. Weiss, D. J. (2002), Mole. Therapy, 6 (2): 148-152.
16. Sharp, P. A. (2001), Genes & Development, 15: 485-490.
17. Tuschl, T. (2001), Chembiochem, 2: 239-245.
18. Elbashir, S. M. et al, 2001, Duplexes of 21-nucleotide RNAs mediate RNA interference in cultured mammalian cells, Nature, 411: 494-498.
19. Schiwarz, D. S. et al, (2003), Cell, 115: 199-208.
20. Khvorova, A. et al, (2003), Cell, 115: 209-216.
21. Reynolds, A. et al, (2004), Nat. Biotechnology, 22: 326-330.
22. McCaffrey, A. P., et al (2002), Nature, 418: 38-39.
23. Gehlbach, P, et al, (2003), Hum. Gene Ther, 14: 129-141.
24. Pierce, E. A., et al, (1995), PNAS, 905-909.
25. Tobe, T, et al, (1998) Am J. Path., 153(5):1641-1646.
26. Zheng, M., Klinman, D. M., Gierynska, M., and Rouse, B. T. (2002), *PNAS* 99, 8944-8949.
27. Zheng M, et al, (2001), *J Virol,* 75, 9828-9835
28. Zhang, L. A. J. Mixson, et al (2002), *Cancer Res.,* 62(19), 5463
29. Tuschl, T. (2002), Nat. Biotech. 20: 446-448
30. Shuldiner, A. R. & Huang, Z. (1995), in *Reverse Transcriptase PCR*, Larrick J. W. & Siebert P. D. (Ellis Horwood) pp. 50-60.
31. Hart, S. L., et al, (1994), *JBC* 269, 12468-12474.
32. Hood, H. D., et al (2002), *Science* 296, 2402-2407.
33. Pasqualini, R. et al, (1996), Nature, 380 (6572), 364-366.
34. Arap, W, et al, (1998), Science, 279: 377-380.
35. Braasch, D. et al (2004), Bioorganic and Medicinal Chemistry Letters, 14: 1139-1143.
36. Woodle, et al, (2001), J. Controlled Release, 74, 309-311.
37. Leng, Q. J. and Mixson A. J. Small interfering RNA targeting Raf-1 inhibits tumor growth in vitro and in vivo. *Cancer Gene Therapy.* (2005), 1-9.
38. Kim, B. et al. (2004) Inhibition of ocular angiogenesis by siRNA targeting vascular endothelial growth factor-pathway genes; therapeutic strategy for herpetic stromal keratitis. *Am. J. Pathol.* 165 (6): 2177-85.

All publications, including issued patents and published patent applications, and all database entries identified by url addresses or accession numbers are incorporated herein by reference in their entirety.

Although this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated siRNA selected from the group consisting of:
   5'-r(CCUGUGGCUACAAGUUCCACCAGCA)-3' (SEQ ID NO. 62) (sense strand sequence, Raf-1), and
   5'-r(CACUACAAAGAACUGGAGUUCCAGA)-3' (SEQ ID NO. 94) (sense strand sequence, mTOR).

2. The siRNA molecule of claim 1 wherein said siRNA molecule binds to both a human mRNA molecule and a homologous mouse mRNA molecule.

3. A composition comprising the siRNA molecule of claim 1 and a pharmaceutically acceptable carrier.

4. A composition comprising the three different isolated siRNA molecules selected from the group consisting of:
   5'-r(CCUGUGGCUACAAGUUCCACCAGCA)-3' (SEQ ID NO. 62) (sense strand sequence, Raf-1),
   5'-r(CACUACAAAGAACUGGAGUUCCAGA)-3' (SEQ ID NO. 94) (sense strand sequence, mTOR), and
   5'-r(GAUCAUGGUCAAGUGCUGGAUGAUA)-3' (SEQ ID NO. 38) (sense strand sequence, EGFR)
   and a pharmaceutically acceptable carrier.

5. The composition of claim 4 comprising the three different isolated siRNA molecules at a ratio of 1:1:1, 1:1.5:0.5, or 0.5:0.5:2.

6. The composition claim 4 wherein said carrier comprises at least one of the following: saline, a sugar, a polypeptide, a polymer, a lipid, a cream, a gel, a micelle material, and a metal nanoparticle.

7. The composition of claim 4 wherein said carrier comprises a histidine-lysine copolymer that forms a nanoparticle with the siRNA molecules.

8. The composition of claim 4 further comprising a therapeutic agent that impedes or blocks tumorigenesis, angiogenesis, cell proliferation, or anti-apoptosis in the breast tissue of a mammal.

9. A nanoparticle comprising the siRNA molecule of claim 1, a carrier, and a targeting ligand.

10. A nanoparticle comprising the three different isolated siRNA molecules selected from the group consisting of:
    5'-r(CCUGUGGCUACAAGUUCCACCAGCA)-3' (SEQ ID NO. 62) (sense strand sequence, Raf-1),
    5'-r(CACUACAAAGAACUGGAGUUCCAGA)-3' (SEQ ID NO. 94) (sense strand sequence, mTOR), and
    5'-r(GAUCAUGGUCAAGUGCUGGAUGAUA)-3' (SEQ ID NO. 38) (sense strand sequence, EGFR),
    a carrier, and a targeting ligand.

11. An isolated 25 mer siRNA molecule selected from the group consisting of a molecule that binds to an mRNA molecule that encodes human Raf-1 and binds to an mRNA molecule that encodes mouse Raf-1; and a molecule that binds to an mRNA molecule that encodes human mTOR and binds to an mRNA molecule that encodes mouse mTOR wherein said molecule is selected from the group consisting of:
    5'-r(CCUGUGGCUACAAGUUCCACCAGCA)-3' (SEQ ID NO. 62) (sense strand sequence, Raf-1), and
    5'-r(CACUACAAAGAACUGGAGUUCCAGA)-3' (SEQ ID NO. 94) (sense strand sequence, mTOR).

12. A composition comprising the three different isolated 25 mer siRNA molecules selected from the group consisting of a molecule that binds to an mRNA molecule that encodes human EGFR and binds to an mRNA molecule that encodes mouse EGFR; a molecule that binds to an mRNA molecule that encodes human Raf-1 and binds to an mRNA molecule that encodes mouse Raf-1; and a molecule that binds to an mRNA molecule that encodes human mTOR and binds to an mRNA molecule that encodes mouse mTOR, wherein said molecule is selected from the group consisting of:
    5'-r(GAUCAUGGUCAAGUGCUGGAUGAUA)-3' (SEQ ID NO. 38) (sense strand sequence, EGFR),
    5'-r(CCUGUGGCUACAAGUUCCACCAGCA)-3' (SEQ ID NO. 62) (sense strand sequence, Raf-1), and
    5'-r(CACUACAAAGAACUGGAGUUCCAGA)-3' (SEQ ID NO. 94) (sense strand sequence, mTOR)
    and a pharmaceutically acceptable carrier.

* * * * *

SEQUENCE LISTING

```
<160> NUMBER OF SEQ ID NOS: 204

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gccugcugcu ccucggcugc ggaua                                               25

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ggucuggugc cuggucugau gaugu                                               25

<210> SEQ ID NO 3
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cuguagacac acccacccac auaca                                               25

<210> SEQ ID NO 4
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 4
uguauguggg ugggugeguguc uacag                                              25

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ccaucgaugu cuacaugauc auggu                                               25

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
accaugauca uguagacauc gaugg                                               25

<210> SEQ ID NO 7
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
acaucaucag accaggcacc agacc                                               25

<210> SEQ ID NO 8
<211> LENGTH: 10
<212> TYPE: PRT
<213> ORGANISM: Unknown
<220> FEATURE:
<223> OTHER INFORMATION: Description of Unknown: RGD peptide

<400> SEQUENCE: 8

Ala Cys Arg Gly Asp Met Phe Gly Cys Ala
1               5                   10

<210> SEQ ID NO 9
<211> LENGTH: 29
<212> TYPE: PRT
<213> ORGANISM: Unknown
<220> FEATURE:
<223> OTHER INFORMATION: Description of Unknown: RVG peptide

<400> SEQUENCE: 9

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 10
<211> LENGTH: 12
<212> TYPE: PRT
```

```
<213> ORGANISM: Unknown
<220> FEATURE:
<223> OTHER INFORMATION: Description of Unknown: FROP peptide

<400> SEQUENCE: 10

Glu Asp Tyr Glu Leu Met Asp Leu Leu Ala Tyr Leu
1               5                   10

<210> SEQ ID NO 11
<211> LENGTH: 9
<212> TYPE: PRT
<213> ORGANISM: Unknown
<220> FEATURE:
<223> OTHER INFORMATION: Description of Unknown: RGD peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (4)..(4)
<223> OTHER INFORMATION: May or may not be present

<400> SEQUENCE: 11

Asp Cys Arg Asp Trp Lys Thr Cys Thr
1               5

<210> SEQ ID NO 12
<211> LENGTH: 41
<212> TYPE: PRT
<213> ORGANISM: Unknown
<220> FEATURE:
<223> OTHER INFORMATION: Description of Unknown: RVG peptide

<400> SEQUENCE: 12

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Arg Arg Arg Arg Arg Arg Arg Arg Arg
        35                  40

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cccugacuac cagcaggacu u                                              21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cugacuacca gcaggacuuc u                                              21

<210> SEQ ID NO 15
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 15
cagggggaug aaagaaugca u                                              21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gggggaugaa agaaugcauu u                                              21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gaauucucca aaauggcccg a                                              21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ccaucgaugu cuacaugauc a                                              21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gaucaugguc aagugcugga u                                              21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cgaugucuac augaucaugg u                                              21

<210> SEQ ID NO 21
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 21
caaagugccu aucaagugga u                                                      21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cuggauccca gaaggugaga a                                                      21

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gacaacccug acuaccagca gga                                                    23

<210> SEQ ID NO 24
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
caacccugac uaccagcagg acu                                                    23

<210> SEQ ID NO 25
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
cccugacuac cagcaggacu ucu                                                    23

<210> SEQ ID NO 26
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26 caggggaug aaagaaugca uuu                                                     23

<210> SEQ ID NO 27
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 27
ggaugaaaga augcauuugc caa                                              23

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gaauucucca aaauggcccg aga                                              23

<210> SEQ ID NO 29
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
cgaugucuac augaucaugg uca                                              23

<210> SEQ ID NO 30
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cuacaugauc auggucaagu gcu                                              23

<210> SEQ ID NO 31
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ggcaaagugc cuaucaagug gau                                              23

<210> SEQ ID NO 32
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cucuggaucc cagaagguga gaa                                              23

<210> SEQ ID NO 33
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 33
gacaacccug acuaccagca ggacu                                              25

<210> SEQ ID NO 34
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ggggaugaaa gaaugcauuu gccaa                                              25

<210> SEQ ID NO 35
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ccaucgaugu cuacaugauc auggu                                              25

<210> SEQ ID NO 36
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gaugucuaca ugaucauggu caagu                                              25

<210> SEQ ID NO 37
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gucuacauga ucauggucaa gugcu                                              25

<210> SEQ ID NO 38
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gaucaugguc aagugcugga ugaua                                              25

<210> SEQ ID NO 39
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 39
gaucacagau uugggcugg ccaaa                                          25

<210> SEQ ID NO 40
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cagauuuugg gcuggccaaa cugcu                                         25

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ggcccugaag gugcgggguc u                                             21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cacugccugg gacacagcca u                                             21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cugaccaugc acaauuuugu a                                             21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ccaugcacaa uuuuguacgg a                                             21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 45
caugcacaau uuuguacgga a                                           21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cugugacuuc ugccuuaagu u                                           21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cugccuuaag uuucuguucc a                                           21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ggaagucccc acauuccaag u                                           21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gaggaagucc ccacauucca a                                           21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
gauccguaug caggacccga a                                           21

<210> SEQ ID NO 51
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51

```
gucacugccu gggacacagc cau                                           23
```

<210> SEQ ID NO 52
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52

```
gaccaugcac aauuuuguac gga                                           23
```

<210> SEQ ID NO 53
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53

```
caugcacaau uuuguacgga aga                                           23
```

<210> SEQ ID NO 54
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54

```
guggcuacaa guuccaccag cau                                           23
```

<210> SEQ ID NO 55
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55

```
cuacaaguuc caccagcauu guu                                           23
```

<210> SEQ ID NO 56
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56

```
caaguuccac cagcauuguu ccu                                           23
```

<210> SEQ ID NO 57
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
caccagcauu guuccuccaa ggu                                              23

<210> SEQ ID NO 58
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gaggaagucc ccacauucca agu                                              23

<210> SEQ ID NO 59
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59 ccuggguac cgggacucag gcu                                               23

<210> SEQ ID NO 60
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ggugauccgu augcaggacc cga                                              23

<210> SEQ ID NO 61
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
cugaccaugc acaauuuugu acgga                                            25

<210> SEQ ID NO 62
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ccuguggcua caaguuccac cagca                                            25

<210> SEQ ID NO 63
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ggcuacaagu uccaccagca uuguu                                            25

```
<210> SEQ ID NO 64
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
gggaggaagu ccccacauuc caagu                                               25

<210> SEQ ID NO 65
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
gugaagaacc uggggguaccg ggacu                                              25

<210> SEQ ID NO 66
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
cagcauuguu ccuccaaggu cccca                                               25

<210> SEQ ID NO 67
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67 ccuggggguac cgggacucag gcuau                                              25

<210> SEQ ID NO 68
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gaggugaucc guaugcagga cccga                                               25

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gccgaagccg cgcgaaccuc a                                                   21
```

```
<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gccgcgcgaa ccucagggca a                                               21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gaggagucua cucgcuucua u                                               21

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gguuuccagc ucagaugcca a                                               21

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
gcucagaugc caaugagagg a                                               21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
cagcauggag ggagagcguc u                                               21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ggugugccag ugggugcuga a                                               21
```

```
<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
gguguccuuu gugaagagcc a                                              21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
ccagcuguuu ggcgccaacc u                                              21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gccagggauc ucuucaaugc u                                              21

<210> SEQ ID NO 79
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gccgcgcgaa ccucagggca aga                                            23

<210> SEQ ID NO 80
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gaggagucua cucgcuucua uga                                            23

<210> SEQ ID NO 81
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
guuuccagcu cagaugccaa uga                                            23

<210> SEQ ID NO 82
```

<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
cagcucagau gccaaugaga gga                                              23

<210> SEQ ID NO 83
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
cagcauggag ggagagcguc uga                                              23

<210> SEQ ID NO 84
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
caggccauca ccuucaucuu caa                                              23

<210> SEQ ID NO 85
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gguguccuuu gugaagagcc aca                                              23

<210> SEQ ID NO 86
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
cacuacaaag aacuggaguu cca                                              23

<210> SEQ ID NO 87
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gccaugaaac acuuuggaga gcu                                              23

<210> SEQ ID NO 88
<211> LENGTH: 23

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
gagguuaucc aguacaaacu ugu                                              23

<210> SEQ ID NO 89
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
gcgcgaaccu cagggcaaga ugcuu                                            25

<210> SEQ ID NO 90
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
guuuccagcu cagaugccaa ugaga                                            25

<210> SEQ ID NO 91
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
cagcauggag ggagagcguc ugaga                                            25

<210> SEQ ID NO 92
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
caggccauca ccuucaucuu caagu                                            25

<210> SEQ ID NO 93
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
ccagcuguuu ggcgccaacc uggau                                            25

<210> SEQ ID NO 94
<211> LENGTH: 25
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 94
cacuacaaag aacuggaguu ccaga                                              25

<210> SEQ ID NO 95
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
gccaugguuu cuugccacau gcugu                                              25

<210> SEQ ID NO 96
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ggucccuugu ggucagcccu cauga                                              25

<210> SEQ ID NO 97
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
cugcgucaug ccagcggggc caaca                                              25

<210> SEQ ID NO 98
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gguuugauua uggucacugg ccaga                                              25

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
gugugcgcag acagugcucc a                                                  21

<210> SEQ ID NO 100
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 100
ccaccaugcc aagugguccc a                                                21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ccugguggac aucuuccagg a                                                21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gcacauagga gaugagcu u                                                  21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
caagauccgc agacguguaa a                                                21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
ggcgaggcag cuugaguuaa a                                                21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
cuugaguuaa acgaacguac u                                                21

<210> SEQ ID NO 106
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 106
ggaaggagcc ucccucaggg u                                              21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
cacuuugggu ccggagggcg a                                              21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
caguauucuu gguuaauauu u                                              21

<210> SEQ ID NO 109
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gccuccgaaa ccaugaacuu ucu                                            23

<210> SEQ ID NO 110
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
cuccaccaug ccaagugguc cca                                            23

<210> SEQ ID NO 111
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
ccugguggac aucuuccagg agu                                            23

<210> SEQ ID NO 112
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 112
cagcacauag gagagaugag cuu                                          23

<210> SEQ ID NO 113
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gcuugaguua aacgaacgua cuu                                          23

<210> SEQ ID NO 114
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
guuaaacgaa cguacuugca gau                                          23

<210> SEQ ID NO 115
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
ggaaggagcc ucccucaggg uuu                                          23

<210> SEQ ID NO 116
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
cucccucagg guuucgggaa cca                                          23

<210> SEQ ID NO 117
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
cuaauguuau uggugucuuc acu                                          23

<210> SEQ ID NO 118
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 118
gagaaagugu uuuauauacg gua                                              23

<210> SEQ ID NO 119
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
ccuccgaaac caugaacuuu cugcu                                            25

<210> SEQ ID NO 120
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
ccaccaugcc aagugguccc aggcu                                            25

<210> SEQ ID NO 121
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
cccuggugga caucuuccag gagua                                            25

<210> SEQ ID NO 122
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gauccgcaga cguguaaaug uuccu                                            25

<210> SEQ ID NO 123
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
cgcagacgug uaaauguucc ugcaa                                            25

<210> SEQ ID NO 124
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 124
guaaauguuc cugcaaaaac acaga                                                 25

<210> SEQ ID NO 125
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
cagcuugagu uaaacgaacg uacuu                                                 25

<210> SEQ ID NO 126
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
guuaaacgaa cguacuugca gaugu                                                 25

<210> SEQ ID NO 127
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ccaugccaag uggucccagg cugca                                                 25

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
guucugaacg ucgaaaagaa a                                                     21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gaaguuuuuu augagcuugc u                                                     21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
gagcuugcuc aucaguugcc a                                              21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
caguacagga ugcuugccaa a                                              21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
gcucccuaua ucccaaugga u                                              21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
cuggacacag uguguuugau u                                              21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
cacagugugu uugauuuuac u                                              21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
guggauuacc acagcugacc a                                              21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136

```
cagaaaccua cugcagggug a                                             21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
ggugaagaau uacucagagc u                                             21

<210> SEQ ID NO 138
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
cugaacgucg aaaagaaaag ucu                                           23

<210> SEQ ID NO 139
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gaaguuuuuu augagcuugc uca                                           23

<210> SEQ ID NO 140
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gagcuugcuc aucaguugcc acu                                           23

<210> SEQ ID NO 141
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gacaguacag gaugcuugcc aaa                                           23

<210> SEQ ID NO 142
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
gaacuaacug gacacagugu guu                                           23
```

```
<210> SEQ ID NO 143
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
cacagugugu uugauuuuac uca                                              23

<210> SEQ ID NO 144
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
gacacagugu guuugauuuu acu                                              23

<210> SEQ ID NO 145
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
cucauccaug ugaccaugag gaa                                              23

<210> SEQ ID NO 146
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
gaccaugagg aaaugagaga aau                                              23

<210> SEQ ID NO 147
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
gagaaaugcu uacacacaga aau                                              23

<210> SEQ ID NO 148
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
guuuuuuaug agcuugcuca ucagu                                            25
```

<210> SEQ ID NO 149
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
gacacagugu guuugauuuu acuca                                              25

<210> SEQ ID NO 150
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
caggacagua caggaugcuu gccaa                                              25

<210> SEQ ID NO 151
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
cucauccaug ugaccaugag gaaau                                              25

<210> SEQ ID NO 152
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
caugugacca ugaggaaaug agaga                                              25

<210> SEQ ID NO 153
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
ccaugaggaa augagagaaa ugcuu                                              25

<210> SEQ ID NO 154
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gagagaaaug cuuacacaca gaaau                                              25

```
<210> SEQ ID NO 155
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ccgcucaauu uaugaauauu aucau                                      25

<210> SEQ ID NO 156
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
cucaauuuau gaauauuauc augcu                                      25

<210> SEQ ID NO 157
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ggaugcuugc caaaagaggu ggaua                                      25

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ctgcctggcc tgcctccact t                                          21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ctgcgggagc tgcagcttcg a                                          21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cctggcctgc ctccacttca a                                          21

<210> SEQ ID NO 161
```

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 161
ccaggagttt gctggctgca a                                        21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 162
ggagtttgct ggctgcaaga a                                        21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
gctggctgca agaagatctt t                                        21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 164
caagaagatc tttgggagcc t                                        21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 165
gatctttggg agcctggcat t                                        21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 166
gatcacaggt tacctataca t                                        21

<210> SEQ ID NO 167
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ggcccaccca gtgtgtcaac t                                              21

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ctgcctggcc tgcctccact tca                                            23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gactgcctgg cctgcctcca ctt                                            23

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ccaggagttt gctggctgca aga                                            23

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gaagatcttt gggagcctgg cat                                            23

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gagatcacag gttacctata cat                                            23

<210> SEQ ID NO 173
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 173
ccagggccca cccagtgtgt caa                                          23

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gcccacccag tgtgtcaact gca                                          23

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gacacagctt atgccctatg gct                                          23

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
cagattgcca agggatgag cta                                           23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gccaagggga tgagctacct gga                                          23

<210> SEQ ID NO 178
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ctgactgcct ggcctgcctc cactt                                        25

<210> SEQ ID NO 179
<211> LENGTH: 25
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 179
gactgcctgg cctgcctcca cttca                                               25

<210> SEQ ID NO 180
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
caggagtttg ctggctgcaa gaaga                                               25

<210> SEQ ID NO 181
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gtttgctggc tgcaagaaga tcttt                                               25

<210> SEQ ID NO 182
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
gctgcaagaa gatctttggg agcct                                               25

<210> SEQ ID NO 183
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gaagatcttt gggagcctgg cattt                                               25

<210> SEQ ID NO 184
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ccagggccca cccagtgtgt caact                                               25

<210> SEQ ID NO 185
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 185
gggcccaccc agtgtgtcaa ctgca                                              25

<210> SEQ ID NO 186
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cacagcttat gccctatggc tgcct                                              25

<210> SEQ ID NO 187
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gatgggggca aggtgcccat caagt                                              25

<210> SEQ ID NO 188
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188 ccaguuggu gucgcggagc acgga                                               25

<210> SEQ ID NO 189
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gaggagccuu caggauuaca agauu                                              25

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gttctccgtg agctggccat ca                                                 22

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                            primer

<400> SEQUENCE: 191
cttctctcag acgctctccc a                                              21

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
caggactgct gtgtggtcta                                                20

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
ggcggttggt actcatgtca a                                              21

<210> SEQ ID NO 194
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
ctctggatcc cagaaggtga ga                                             22

<210> SEQ ID NO 195
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gccatccact tgataggcac tt                                             22

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gaaggaagag gagaggggc cgca                                            24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<210> SEQ ID NO 198
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gcctggcctg cctccacttc aa                                            22

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
gccaggctcc caaagatctt ct                                            22

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Lys His His His Lys His His His Lys His His His Lys His His
1               5                   10                  15

His

<210> SEQ ID NO 201
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Lys His His His Lys His His His Lys Gly His His His Lys His His
1               5                   10                  15

His Gly

<210> SEQ ID NO 202
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

His His His Lys
1

<210> SEQ ID NO 203

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Lys His His Lys His His His Lys His His His Lys His His
1               5                   10                  15

Lys

<210> SEQ ID NO 204
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Lys His His Lys His His His Asn His His Asn His His
1               5                   10                  15

Asn
```